United States Patent
Kurland et al.

(10) Patent No.: US 10,914,741 B2
(45) Date of Patent: Feb. 9, 2021

(54) USE OF 13C AND 15N DERIVATIZATION REAGENTS FOR GAS AND LIQUID CHROMATOGRAPHY-MASS SPECTROSCOPY CHEMICAL IDENTIFICATION AND QUANTIFICATION

(71) Applicant: Albert Einstein College of Medicine, Bronx, NY (US)

(72) Inventors: Irwin J. Kurland, Lloyd Harbor, NY (US); Yunping Qiu, Pelham Manor, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 462 days.

(21) Appl. No.: 15/967,616

(22) Filed: May 1, 2018

(65) Prior Publication Data

US 2018/0275138 A1    Sep. 27, 2018

Related U.S. Application Data

(63) Continuation-in-part of application No. PCT/US2016/059813, filed on Nov. 1, 2016.

(60) Provisional application No. 62/249,981, filed on Nov. 3, 2015.

(51) Int. Cl.
*G01N 33/68* (2006.01)

(52) U.S. Cl.
CPC ..... *G01N 33/6848* (2013.01); *G01N 2458/15* (2013.01); *G01N 2458/20* (2013.01)

(58) Field of Classification Search
None
See application file for complete search history.

(56) References Cited

U.S. PATENT DOCUMENTS

| | | | | |
|---|---|---|---|---|
| 7,494,822 B2 * | 2/2009 | Nguyen | ............ | G01N 30/7206 436/129 |
| 2006/0200316 A1 | 9/2006 | Kanani et al. | | |
| 2014/0296339 A1 | 10/2014 | Gant et al. | | |

OTHER PUBLICATIONS

Koek, M.M. et al. Quantitative metabolomics based on gas chromatography mass spectrometry: status and perspectives, Metabolomics, vol. 7, pp. 307-328 (Year: 2011).*
PCT International Search Report and Written Opinion dated Dec. 29, 2016 for PCT International Patent Application No. PCT/US2016/059813, 7 pages.
Tang et al., "Advances in Analysis of Microbial Metabolic Fluxes via 13C Isotopic Labeling," Mass Spectrometry Reviews, Nov. 24, 2008, pp. 362-375. Reviews,.
Simon-Manso et al., Metabolite Profiling of a NIST Standard Reference for Human Plasma (SRM 1950)—GC-MS, LC-MS, NMR, and Clinical Laboratory Analyses, Libraries and Web-based Resources, Analytical Chemistry, Oct. 22, 2013, pp. 1-21.

* cited by examiner

*Primary Examiner* — Xiaoyun R Xu
(74) *Attorney, Agent, or Firm* — Fox Rothschild LLP

(57) ABSTRACT

Disclosed are $^{13}$C and $^{15}$N derivatization reagents and their use for gas chromatography-mass spectroscopy and liquid chromatography/mass spectroscopy chemical identification and quantification.

14 Claims, 15 Drawing Sheets

(mainlib) D-Allose, aldononitrile, pentaacetate

Derivatize the experiment with $^{13}$C BSTFA, or $^{13}$C MTBSTFA vs. matching unlabeled derivatization silylation reagents
Calculate the number of chemical groups on the molecule that can be silylated, using chemical ionization (CI) and high resolution GC/MS, from the mass shift from unlabeled reagents, aided globally from the exact registration of peaks between labeled and unlabeled reagents
Narrow the chemical formulae possible for the metabolites not in a database
Comparison of EI spectra from matching unlabeled and labeled $^{13}$C silylation reagents can reveal composition of EI fragment identity to further aid chemical formulae identification

If amino group numbers need to be confirmed for an unknown metabolite
Derivatize the experimental group containing the unknown with 99% $^{13}$C methylchloroformate (MCF) and unlabeled methanol vs unlabeled MCF/methanol
Each 2 dalton mass shift seen on CI for each unknown represents one amino group
Comparison of EI spectra from matching unlabeled and labeled derivatization reagents can reveal composition of EI fragment identity to further aid chemical formulae identification
Compare spectra with that from sample derivatized with unlabeled silylation reagents to further narrow chemical formulae

If carbonyl group numbers need to be confirmed for an unknown metabolite
Derivatize the experimental group containing the unknown with unlabeled methylchloroformate and 99% $^{13}$C methanol vs unlabeled MCF/methanol
Each dalton mass shift seen on CI for each unknown represents one carbonyl group
Comparison of EI spectra from matching unlabeled and labeled derivatization reagents can reveal composition of EI fragment identity to further aid chemical formulae identification
Compare spectra with that from sample derivatized with unlabeled silylation and/or MCF reagents to further narrow chemical formulae

If hydroxyl group numbers need to be confirmed for an unknown metabolite
Derivatize the experimental group containing the unknown with 99% $^{13}$C acetic anhydride vs. unlabeled acetic anhydride.
Each dalton mass shift on CI for each unknown represents one hydroxyl group
Comparison of EI spectra from matching unlabeled and labeled derivatization reagents can reveal composition of EI fragment identity to further aid chemical formulae identification
Compare spectra with that from sample derivatized with unlabeled silylation and/or MCF and methanol reagents to further narrow chemical formulae

FIG. 7A

Mass spectrum of PITC derivatized alanine

USE OF 13C AND 15N DERIVATIZATION REAGENTS FOR GAS AND LIQUID CHROMATOGRAPHY-MASS SPECTROSCOPY CHEMICAL IDENTIFICATION AND QUANTIFICATION

CROSS-REFERENCE TO RELATED APPLICATIONS

This application is a continuation-in-part of and claims priority of PCT International Patent Application No. PCT/US2016/059813, filed Nov. 1, 2016, which designates the United States of America and which claims the benefit of U.S. Provisional Patent Application No. 62/249,981, filed on Nov. 3, 2015, the contents of which are herein incorporated by reference in their entirety into the present application.

BACKGROUND OF THE INVENTION

Throughout this application various publications are referred to in superscripts. Full citations for these references may be found at the end of the specification. The disclosures of these publications are hereby incorporated by reference in their entirety into the subject application to more fully describe the art to which the subject invention pertains.

Biological samples contain a diverse set of small chemical molecules that is referred to as a metabolome. Gas Chromatography-Mass Spectroscopy (GC/MS) is an under-utilized method for metabolome characterization, in part, due to the need for proficiency in making chemical derivatives of the chemical to be volatilized and examined by GC/MS. The present invention provides reagents and methods that address previously unmet needs in untargeted metabolomic profiling for both GC/MS and liquid chromatography/mass spectrometry (LC/MS) applications.

SUMMARY OF THE INVENTION

The present invention provides a kit for metabolomics/lipidomic profiling comprising one or more of $^{13}C$ methyl-chloroformate, $^{13}C$ ethylchloroformate, $^{13}C$ methanol, $^{13}C$ ethanol, $^{13}C$ acetyl anhydride, $^{13}C$ labeled N,O-bistrifluoroacetamide (BSTFA), $^{13}C$ labeled N-(tert.-butyldimethylsilyl)-N-methyl-trifluoroacetamide (MTBSTFA), trimethylsilyl-$^{13}C$-diazomethane (TMS-$^{13}CHN_2$), $^{13}C$ and $^{15}N$ PITC, $^{13}C$ and $^{15}N$ aniline, and $^{13}C$ and $^{15}N$ O-benzylhydroxylamine. The kit can further contain standards, such as the NIST1950 plasma standard, as well as other standardized tissue extracts or mixtures of metabolites which typify tissue or biofluid metabolite/lipid extracts.

The invention further comprises methods and instructions for use for metabolomics/lipidomic profiling of compounds of known and unknown identities in a biological sample using a Directed Isotopic Positional Derivatization (DIPD) approach that utilizes $^{13}C$ and/or $^{15}N$ derivatization reagents as detailed herein.

BRIEF DESCRIPTION OF THE DRAWINGS

FIG. 7A. Flowchart demonstrating an algorithm for the use of stable isotope reagents to chemically characterize the groups on unknown metabolites for an experiment processed using high resolution GC/MS. Chemical ionization (CI) preserves the molecular ion for chemical formulae calculation, and $^{13}C$ labeling of electron impact ionization (EI) fragments can also help to confirm/narrow possible chemical formulae. The cost of these unknown metabolite characterizations can be minimized by using $^{13}C$ derivatization reagents only for the pooled quality control samples.

DETAILED DESCRIPTION OF THE INVENTION

Figure 1:
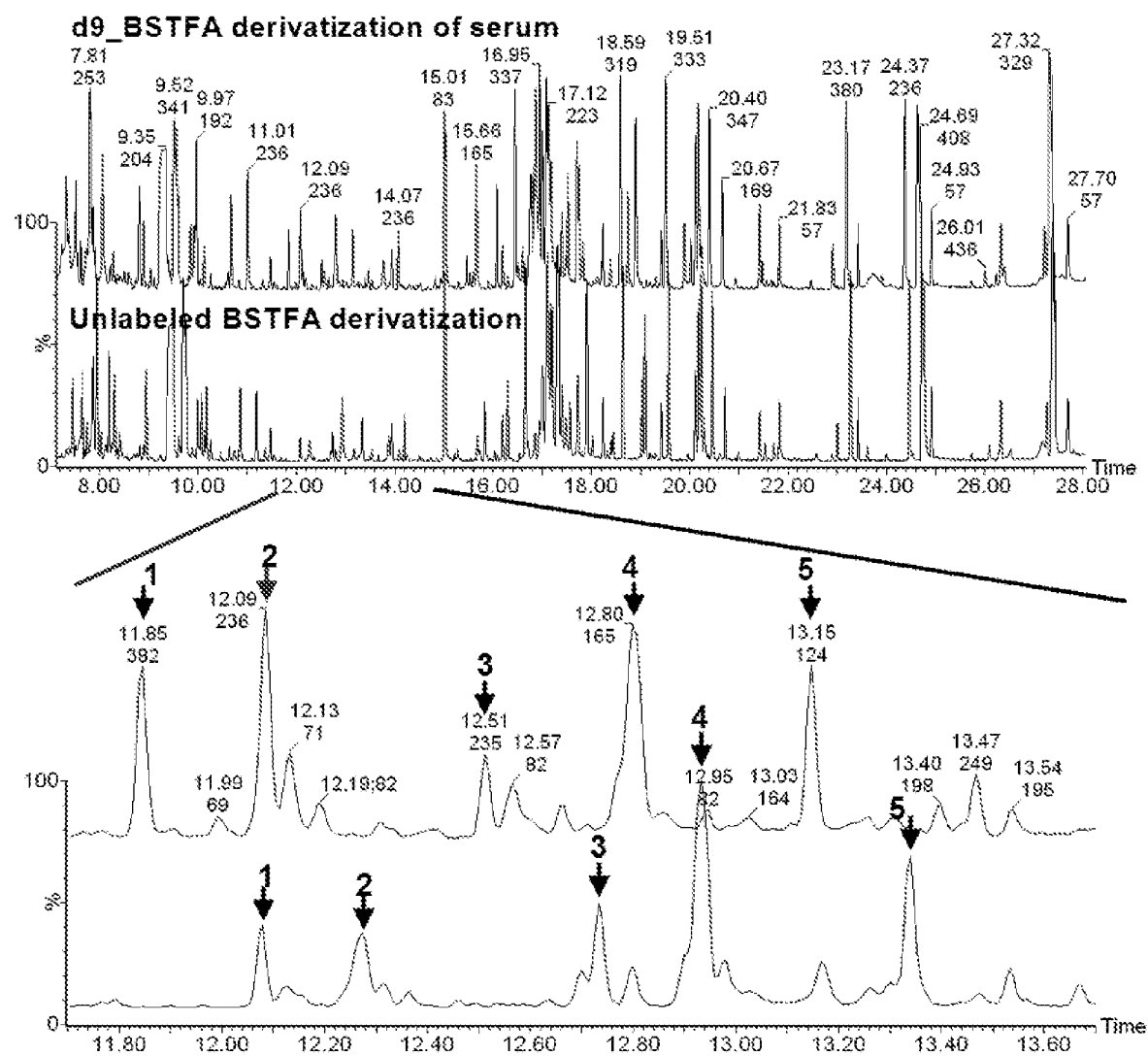
FIG. 1. Disadvantages of deuterated reagent labeling for silylation reagents. Serum was purchased from Santa Cruz. Total ion chromatogram (TIC) in the Electron Impact Ionization (EI) mode reveals that deuterated d9-BSTFA derivatives (upper tracing of pair) have a time shift in comparison to unlabeled BSTFA derivatives (lower tracing of pair), as seen from the sets of peaks, indicated by number for the same pair of arrows, where the arrows in each pair are shifted to the right in the lower tracing. The bottom figure is enlarged between the retention times of 11.8 to 13.6 min.

The present invention provides a kit for metabolomics/lipidomic profiling comprising one or more of $^{13}$C methylchloroformate, $^{13}$C ethylchloroformate, $^{13}$C methanol, $^{13}$C ethanol, $^{13}$C acetyl anhydride, $^{13}$C labeled N,O-bistrifluoroacetamide (BSTFA), $^{13}$C labeled N-(tert.-butyldimethylsilyl)-N-methyl-trifluoroacetamide (MTBSTFA), trimethylsilyl-$^{13}$C-diazomethane (TMS-$^{13}$CHN$_2$), $^{13}$C and $^{15}$N phenylisothiocyanate (PITC), $^{13}$C and $^{15}$N aniline, and $^{13}$C and $^{15}$N O-benzylhydroxylamine (o-BHA). The kit can further contain standards, such as the NIST1950 plasma standard, as well as other standardized tissue extracts or mixtures of metabolites which typify tissue or biofluid metabolite/lipid extracts. The kit can further comprise instructions for use for metabolomics/lipidomic profiling of compounds in a biological sample.

The invention also provides a method for metabolomic/lipidomic profiling of compounds of known and unknown identities in a biological sample using a Directed Isotopic Positional Derivatization (DIPD) approach that utilizes $^{13}$C and/or $^{15}$N derivatization reagents as detailed herein, by:

A) i) derivatizing the one or more compounds with one or more of one or more of $^{13}$C methylchloroformate, $^{13}$C ethylchloroformate, $^{13}$C methanol, $^{13}$C ethanol, $^{13}$C acetyl anhydride, $^{13}$C labeled N,O-bistrifluoroacetamide (BSTFA), $^{13}$C labeled N-(tert.-butyldimethylsilyl)-N-methyl-trifluoroacetamide (MTBSTFA), trimethylsilyl-$^{13}$C-diazomethane (TMS-$^{13}$CHN$_2$) $^{13}$C and $^{15}$N phenylisothiocyanate (PITC), $^{13}$C and $^{15}$N aniline, and $^{13}$C and $^{15}$N O-benzylhydroxylamine (o-BHA) vs. one or more matching unlabeled derivatization reagents; or ii) making one or more GC/MS $^{13}$C labeled DIPD silylation standards for quantitating the one or more compounds by derivatizing one or more compounds in a standardized mix of compounds aimed at reproducing the targeted biofluid or tissue profile, or the QC standard, with trimethylsilyl-$^{13}$C-diazomethane (TMS-$^{13}$CHN$_2$), or acyl chloroformates/alcohols (examples, methyl chloroformate, ethyl chloroformate, methanol, ethanol) and introducing the $^{13}$C labeled silylation standard into a compound sample derivatized with unlabeled or singly labeled DIPD reagents for GC/MS (TMS-$^{13}$CHN$_2$, methyl chloroformate, ethyl chloroformate, methanol, ethanol, current examples); or iii) making one or more LC/MS $^{13}$C and/or $^{15}$N$_1$ labeled DIPD standards for quantitating the one or more compounds by derivatizing one or more compounds in a standardized mix of compounds aimed at reproducing the targeted biofluid or tissue profile, or the QC standard, with $^{13}$C and $^{15}$N phenylisothiocyanate (PITC), and $^{13}$C and $^{15}$N aniline, and $^{13}$C and $^{15}$N O-benzylhydroxylamine (o-BHA), and introducing the $^{13}$C and/or $^{15}$N$_1$ labeled standard into a compound sample derivatized with unlabeled or singly labeled DIPD reagents (aniline, PITC and o-BHA, as current examples);

and, for i) or ii) or iii), calculating the number of chemical groups on the molecule that can be derivatized for gas chromatography-mass spectroscopy (GC/MS) DIPD reagents using chemical ionization (CI) and/or electron impact (EI) ionization and GC/MS, and for LC/MS DIPD reagents (aniline, PITC and o-BHA, as current examples) from the mass shift from unlabeled reagents, aided globally from the exact chromatographic registration of peaks between labeled and unlabeled reagents;

narrowing the chemical formulae possible for compounds not in a database; and for GC/MS comparing electron impact ionization (EI) spectra from matching unlabeled and labeled $^{13}$C silylation reagents to reveal a composition of EI fragment identity to further aid chemical formulae identification; and for LC/MS comparing high mass accuracy (10,000 to 120,000 resolution commonly available) DIPD spectra to identify and quantitate known and unknown metabolites. Identification of unknown metabolites may be aided by ion mobility, to help discern chemical classes, or ultra-high resolution (>240,000 resolving power) mass spectrometers.

B) For GC/MS identifications: i) if metabolites containing amino group need to be identified and/or the number of amino groups confirmed for an unknown compound, derivatizing the compounds containing the unknown with 99% $^{13}$C methylchloroformate (MCF) and unlabeled methanol vs. unlabeled MCF/methanol, wherein each 2 dalton mass shift seen on CI for each unknown represents one amino group;

comparing the EI spectra from matching unlabeled and labeled derivatization reagents to reveal composition of EI fragment identity to further aid chemical formulae identification; and comparing spectra with that from the sample derivatized with unlabeled silylation reagents to further narrow chemical formulae; and/or ii) if carboxyl group numbers need to be confirmed for an unknown compound, derivatizing the compounds containing the unknown with unlabeled methylchloroformate and 99% $^{13}$C methanol vs. unlabeled MCF/methanol, wherein each dalton mass shift seen on CI for each unknown represents one carboxyl group;

comparing EI spectra from matching unlabeled and labeled derivatization reagents to reveal composition of EI fragment identity to further aid chemical formulae identification; and comparing spectra with that from compounds derivatized with unlabeled silylation and/or MCF reagents to further narrow chemical formulae; and/or iii) if hydroxyl group numbers need to be confirmed for an unknown carbohydrate, derivatizing the carbohydrates containing the unknown with 99% $^{13}$C acetic anhydride vs. unlabeled acetic anhydride, wherein each dalton mass shift on CI for each unknown represents one hydroxyl group;

iv) comparing EI spectra from matching unlabeled and labeled derivatization reagents to reveal composition of EI fragment identity to further aid chemical formulae identification; and v) comparing spectra with that from the sample derivatized with unlabeled silylation and/or MCF and methanol reagents to further narrow chemical formulae; and thereby metabolomic/lipidomic profiling one or more compounds in a biological sample.

The method can further comprise determining the number of carbonyl, carboxyl, phosphoryl or amino/amine groups of a compound by assessing the molecular ion and/or MS/MS profiles by LC/MS using DIPD reagents, such as $^{13}$C and $^{15}$N aniline, $^{13}$C and $^{15}$N PITC, and $^{13}$C and $^{15}$N o-BHA.

The one or more unlabeled derivatization silylation reagent can be selected, e.g., from the group consisting of one or more of N,O-bistrifluoroacetamide (BSTFA), N-(tert.-butyldimethylsilyl)-N-methyl-trifluoroacetamide (MTBSTFA), acetic anhydride and N-Methyl-N-(trimethylsilyl) trifluoroacetamide (MSTFA).

For LC/MS identifications:
i) if carboxyl/carbonyl group numbers need to be confirmed for an unknown compound, derivatizing the compounds containing the unknown with $^{13}C_6$ aniline or $^{13}C_6$ O-benzylhydroxylamine (o-BHA) vs. unlabeled aniline or o-BHA, wherein each 6 dalton mass shift seen with the molecular ion for each unknown represents one carboxyl group;

ii) comparing MS/MS spectra from matching unlabeled and labeled derivatization reagents to reveal composition of MS/MS fragment identity to further aid chemical formulae identification. For example for identification of known or unknown metabolites s containing carboxyl groups, with either neutral loss mode on a unit Dalton mass spectrometer, or mining parent/product spectra after MSall on a Sciex Triple TOF, the loss of m/z 124 for unlabeled o-BHA derivatizations, or m/z 130 for $^{13}C_6$ o-BHA, indicates a loss of the (H-1) unlabeled o-BHA (m/z 124), or a loss of the (H-1)$^{13}C_6$ o-BHA (m/z 130);

iii) if metabolites containing amino group need to be identified and/or the number of for an unknown compound, derivatizing the compounds containing the unknown with $^{13}C_6$ phenylisothiocyanate (PITC) vs. unlabeled (natural abundance) PITC, wherein each 6 dalton mass shift seen on CI for each unknown represents one amino group;

comparing the MS/MS spectra from matching unlabeled and labeled derivatization reagents to reveal composition of MS/MS fragment identity to further aid chemical formulae identification; and comparing spectra with $^{13}C_6$ PITC that from the sample derivatized with unlabeled PITC reagents to further narrow chemical formulae; and/or iv) if phosphoryl group numbers need to be confirmed for an unknown compound, derivatizing the compounds containing the unknown with 99% $^{13}C_6$ aniline vs. unlabeled aniline, wherein each 6 dalton mass shift seen with the molecular ion for each unknown represents one carbonyl group;

v) comparing MS/MS spectra from matching unlabeled and labeled derivatization reagents to reveal composition of MS/MS fragment identity to further aid chemical formulae identification;

vi) comparing spectra with that from the sample derivatized with unlabeled DIPD reagents to further narrow chemical formulae; and thereby metabolomic/lipidomic profiling one or more compounds in a biological sample.

Derivatizing compounds with trimethylsilyl-$^{13}$C-diazomethane (TMS-$^{13}CHN_2$) can be used, e.g., in connection with carboxyl and phosphate groups on the compounds. TMS-$^{13}CHN_2$ can be used, e.g., to create a $^{13}$C labeled silylation standard for TMS-$CHN_2$ derivatives of one or more of compounds containing phosphate, COOH, aldehyde and/or amine groups. The one or more compounds can be selected, e.g., from the group consisting of glycolytic intermediates, organic acids/TCA cycle intermediates, amino acids, amines, fatty acids, eicosanoids/prostanoids; phospholipids/sphingolipids; phosphatidylinositol (PtdIns); and phosphorylated phosphoinisitides PtdIns3P, PtdIns4P, PtdIns5P, PtdIns(3,4)P$_2$, PtdIns(3,5)P$_2$, PtdIns(4,5)P$_2$ and PtdIns(3,4,5)P$_3$, phosphatidic acid (PA), phosphatidylserine (PS), phosphatidylcholine (PC), phosphatidylethanolamine (PE), phosphatidylglycerol (PG) and their lysophospholipids counterparts (LPC, -LPE, -LPS, -LPA, -LPG, and -LPI) and sphingomyelin.

In one embodiment, derivatizing compounds with trimethylsilyl-13C-diazomethane (TMS-$^{13}CHN_2$) are used in connection with carboxyl and phosphate groups on the compounds. In one embodiment, the one or more compounds are derivatized with one or more of $^{13}$C N,O-bistrifluoroacetamide (BSTFA), $^{13}$C N-(tert.-butyldimethylsilyl)-N-methyl-trifluoroacetamide (MTBSTFA), and trimethylsilyl-$^{13}$C-diazomethane (TMS-13CHN2) vs. one or more matching unlabeled derivatization silylation reagents.

In one embodiment, the method comprises making one or more $^{13}$C labeled silylation standards for quantitating the one or more compounds by derivatizing the one or more compounds with trimethylsilyl-$^{13}$C-diazomethane (TMS-$^{13}CHN_2$), and introducing the $^{13}$C labeled silylation standard into a compound sample derivatized with unlabeled TMS-CHN2, and optionally then derivatizing these methylated compounds with one or more unlabeled derivatization silylation reagents. The unlabeled derivatization silylation reagent can be selected, e.g., from the group consisting of one or more of N,O-bistrifluoroacetamide (BSTFA), N-(tert.-butyldimethylsilyl)-N-methyl-trifluoroacetamide (MTBSTFA), and N-Methyl-N-(trimethylsilyl) trifluoroacetamide (MSTFA).

Preferably, one or more of amino group numbers are confirmed for an unknown compound, carbonyl group numbers are confirmed for an unknown compound, and hydroxyl group numbers are confirmed for an unknown compound.

In one embodiment, TMS-$^{13}CHN_2$ or other DIPD reagents is used to create a $^{13}$C labeled silylation standard of one or more of compounds containing phosphate, COOH, aldehyde and/or amine groups.

Preferably, the one or more compounds are selected from the group consisting of sugars, glycolytic intermediates, organic acids/TCA cycle intermediates, amino acids, amines, fatty acids, eicosanoids/prostanoids; phospholipids/sphingolipids; phosphatidylinositol (PtdIns); and phosphorylated phosphoinisitides PtdIns3P, PtdIns4P, PtdIns5P, PtdIns(3,4)P2, PtdIns(3,5)P2, PtdIns(4,5)P2 and PtdIns(3,4,5)P3, phosphatidic acid (PA), phosphatidylserine (PS), phosphatidylcholine (PC), phosphatidylethanolamine (PE), phosphatidylglycerol (PG) and their lysophospholipids counterparts (LPC, -LPE, -LPS, -LPA, -LPG, and -LPI) and sphingomyelin.

The invention also provides a method of creating a $^{13}$C labeled methylation standard for Liquid Chromatography-Mass Spectroscopy (LC/MS) identification and quantitation of one or more compounds with phosphate, COOH, aldehyde and/or amine groups, the method comprising derivatizing the one or more compounds with trimethylsilyl-$^{13}$C-diazomethane (TMS-$^{13}CHN_2$) to create an internal standard for LC/MS identification and quantitation. The one or more compounds can be selected, e.g., from the group consisting of glycolytic intermediates, organic acids/TCA cycle intermediates, amino acids, amines, fatty acids, eicosanoids/prostanoids, phospholipids/sphingolipids, phosphatidylinositol (PtdIns); and phosphorylated phosphoinisitides PtdIns3P, PtdIns4P, PtdIns5P, PtdIns(3,4)P$_2$, PtdIns(3,5)P$_2$, PtdIns(4,5)P$_2$ and PtdIns(3,4,5)P$_3$, phosphatidic acid (PA), phosphatidylserine (PS), phosphatidylcholine (PC), phosphatidylethanolamine (PE), phosphatidylglycerol (PG) and their lysophospholipids counterparts (LPC, -LPE, -LPS, -LPA, -LPG, and -LPI) and sphingomyelin.

The invention provides for the determination of the metabolome of any sample and quantification of all the metabolome with stable isotope labeled internal standards derived from labeled derivatization reagents. The invention can globally code large numbers of analytes for comparison between two samples, or a sample and its internal standard (IS) simultaneously, with precise chromatographic retention time registration between the two samples (or IS) and no peak shape changes due to use of $^{13}$C or $^{15}$N labeling for the derivatization reagent, instead of the commonly used deuterium labeling.

Also provided is a kit for metabolomics/lipidomic profiling of known and unknown identities in a biological sample using a Directed Isotopic Positional Derivatization (DIPD) approach which utilizes $^{13}$C and/or $^{15}$N derivatization reagents comprising one or more of $^{13}$C methylchloroformate, $^{13}$C ethylchloroformate, $^{13}$C methanol, $^{13}$C ethanol, $^{13}$C acetyl anhydride, $^{13}$C labeled N,O-bistrifluoroacetamide (BSTFA), $^{13}$C labeled N-(tert.-butyldimethylsilyl)-N-methyl-trifluoroacetamide (MTBSTFA), trimethylsilyl-$^{13}$C-diazomethane (TMS-$^{13}$CHN$_2$), $^{13}$C and $^{15}$N PITC, $^{13}$C and $^{15}$N aniline, and $^{13}$C and $^{15}$N O-benzylhydroxylamine. The kit can further contain standards, such as the NIST1950 plasma standard, as well as other standardized tissue extracts or mixtures of metabolites which typify tissue or biofluid metabolite/lipid extracts. The kit can further comprise instructions for use for metabolomics/lipidomic profiling of compounds in a biological sample.

The user could either use DIPD reagents to $^{13}$C and/or $^{15}$N derivatize label the quality control sample (QC, combined pool of a small fraction of each sample) for all the samples in a run to spike as an internal standard (IS) in each sample, or $^{13}$C and/or $^{15}$N label the NIST1950 plasma standard or other standardized tissue extracts or mixtures of metabolites which typify tissue or biofluid metabolite/lipid extracts for an IS. For GC/MS applications, the $^{13}$C methylchloroformate and $^{13}$C methanol, used together to derivatize the IS, would label all amine and carboxylic acid groups, and another run could be done with $^{13}$C acetic anhydride to label the metabolite hydroxyl groups for metabolites such as sugars. TMS-$^{13}$CHN$_2$ can be used, e.g., to create a $^{13}$C labeled silylation standard for TMS-CHN$_2$ derivatives of one or more of compounds containing phosphate, COOH, aldehyde and/or amine groups. For LC/MS applications, $^{13}$C and $^{15}$N PITC, and $^{13}$C and $^{15}$N aniline, and $^{13}$C and $^{15}$N O-benzylhydroxylamine, can, as described, label carboxyl, carbonyl, phosphoryl and amine groups, as $^{13}$C and/or $^{15}$N IS standards can be made for biofluid or tissue samples. For tissue samples, however the IS in this case would have to be the QC for the tissue samples, or a standardized tissue extract, which would result in normalization of each sample metabolite by the average level of the metabolite in the sample set. As described herein, not only can quantification be done, but the formula of unknown metabolites in the QC sample using chemical ionization (CI) for GC/MS, or the molecular ion for LC/MS, can be determined from comparison of the use of labeled and unlabeled derivatization reagents. The specificity of the derivatization reagents allows more information to be obtained for unknown metabolites. For example, for GC/MS, $^{13}$C acetic anhydride labeling labels only hydroxyl groups. If $^{13}$C methylchloroformate is used with unlabeled methanol for derivatization, only amine groups will be labeled. If $^{13}$C methanol is used with unlabeled methylchloroformate for derivation, only carbonyl groups will be derivatized. For LC/MS, aniline can label carboxyl, carbonyl and phosphoryl groups, o-BHA can label carbonyl and carboxyl groups, and PITC can label amino groups.

A $^{13}$C labeled silylating agent is more powerful than acyl chloroformate/alcohol or acetic anhydride, for quantification, as silylating agents derivatize a broad variety of functional groups ranging from hydroxyl, thiol, amino, and imino groups to carboxyl and phosphate groups. The use of $^{13}$C labeled N-methyl-N-tert-butyldimethylsilyl)-trifluoroacetamide (MTB-STFA) as the silylating agent has an advantage over $^{13}$C BSTFA in that the labeled silylation group is far less likely to hydrolyze, which could cause scrambling of the labeling between differentially coded analytes during gas chromatography. While $^{13}$C silylation reagents could label more metabolites than $^{13}$C chloroformates, alcohols and acetic anhydrides, the chemical identities of the groups silylated is not as easily determined for metabolites/chemicals of unknown identity, and require additional runs with $^{13}$C methylchoroformate/methanol and $^{13}$C acetyl anhydride for confirmation, as well as use of high resolution GC/MS (FIG. 7). TMS-$^{13}$CHN$_2$ has advantages over $^{13}$C methylchoroformate/methanol in that it has a broader range of reactive groups and compounds it can derivatize, and the silylation group in the TMS-$^{13}$CHN$_2$ does not become a part of the compound derivatized, only the methyl group.

This invention will be better understood from the Experimental Details, which follow. However, one skilled in the art will readily appreciate that the specifics discussed are merely illustrative of the invention as described more fully in the claims that follow thereafter.

Experimental Details

Overview

Gas Chromatography-Mass Spectroscopy (GC/MS) is an under-utilized method for metabolome characterization, in part due to the need for proficiency in making chemical derivatives of the chemical to be volatilized and examined by GC/MS. The present invention has both GC/MS and LC/MS applications using specially designed $^{13}$C and/or $^{15}$N Directed Isotopic Positional Derivatization (DIPD) reagents, for identification and quantification of known and unknown metabolites in specific chemical class(es) in global analysis, for a sample. The present data show that for GC/MS $^{13}$C derivation reagents DO NOT HAVE retention time shifts seen with deuterated derivatization reagents, facilitating their use to spike a reference sample, with precise chromatographic time registration, for absolute quantitation and global identification. The invention described herein provides for GC/MS applications the design of $^{13}$C acyl chloroformate derivatization reagents and alcohols (methylchloroformate and methanol discussed in depth) as well as $^{13}$C silylation reagents (N,O-bistrifluoroacetamide [BSTFA], N-(tert.-butyldimethylsilyl)-N-methyl-trifluoroacetamide [MTBSTFA]), TMS-$^{13}$CHN$_2$, $^{13}$C acetic anhydride, and how to utilize these, and other, $^{13}$C derivatization reagents, for quantification and identification of chemicals in a sample. The invention herein also provides for DIPD reagents for LC/MS application, whether for unit Dalton or high mass accuracy applications, $^{13}$C and $^{15}$N phenylisothiocyanate (PITC), and $^{13}$C and $^{15}$N aniline, and $^{13}$C and $^{15}$N O-benzylhydroxylamine (o-BHA), which can, label carboxyl, carbonyl, phosphoryl and amine groups on known and unknown metabolites/chemicals, as well as make $^{13}$C and/or $^{15}$N IS standards for biofluid or tissue sample quantification assessments.

The DIPD approach is novel, and differs uniquely from the present state of the art. Both the QDA labeling reagent of Higashi and Fan [2] and the dansyl chloride labeling reagent of Li[3,4] yield patterns no different than the top panels (normal patterns) of FIGS. 3E, 7D, 7G and 7I. The M1/M0 and Mn−1/Mn DIPD barcode patterns allows greatly improved discrimination and selectivity by chemical class derivatized (see FIG. 7G for the LC/MS aniline DIPD barcode alanine mass spectrum, and FIG. 7I for theo-BHA DIPD barcode a-KG mass spectrum). LC/MS systems that allow global mining of parent and product ion data, such as the Sciex Triple TOF MS/MS$^{ALL}$ with SWATH acquisition mode, would allow the confirmative recognition of M1/M0 and Mn−1/Mn DIPD barcode patterns, as all the M1/M0 and Mn−1/Mn DIPD spectra could be found within one SWATH window, and molecular ion and characteristic fragments for the DIPD reagent used (see FIG. 7H for o-BHA) would be seen. $^{13}$C aniline derivatization used for short chain fatty acid quantitation in stool by Chan et al.[5] was simply used to derive SCFA quantitation standards, not search for unknown chemical identifications.

The invention provides a combination of a diagnostic device and Directed Isotopic Positional Derivatization (DIPD) reagents specific for chemical group identification on a chemical/metabolite, and an algorithm for interpreting the mass spectra for quantitation and identification. The algorithm can be incorporated into a software program for higher throughput identifications. The invention provides 1) formulation of $^{13}$C and/or $^{15}$N$_1$ labeled Directed Isotopic Positional Derivatization reagent classes, 2) scientific applications and commercial advantages of having these $^{13}$C and/or $^{15}$N$_1$ derivatization reagents for chemical identifications/characterizations, and quantitation under both unit dalton and high mass accuracy mass spectroscopy; and 3) algorithms for unknown chemical identification using combinations of unlabeled and labeled derivatization reagents, and the molecular ion of the DIPD derivatized compounds and their compounds DIPD fragmentation products.

Experimental

Figure 2:
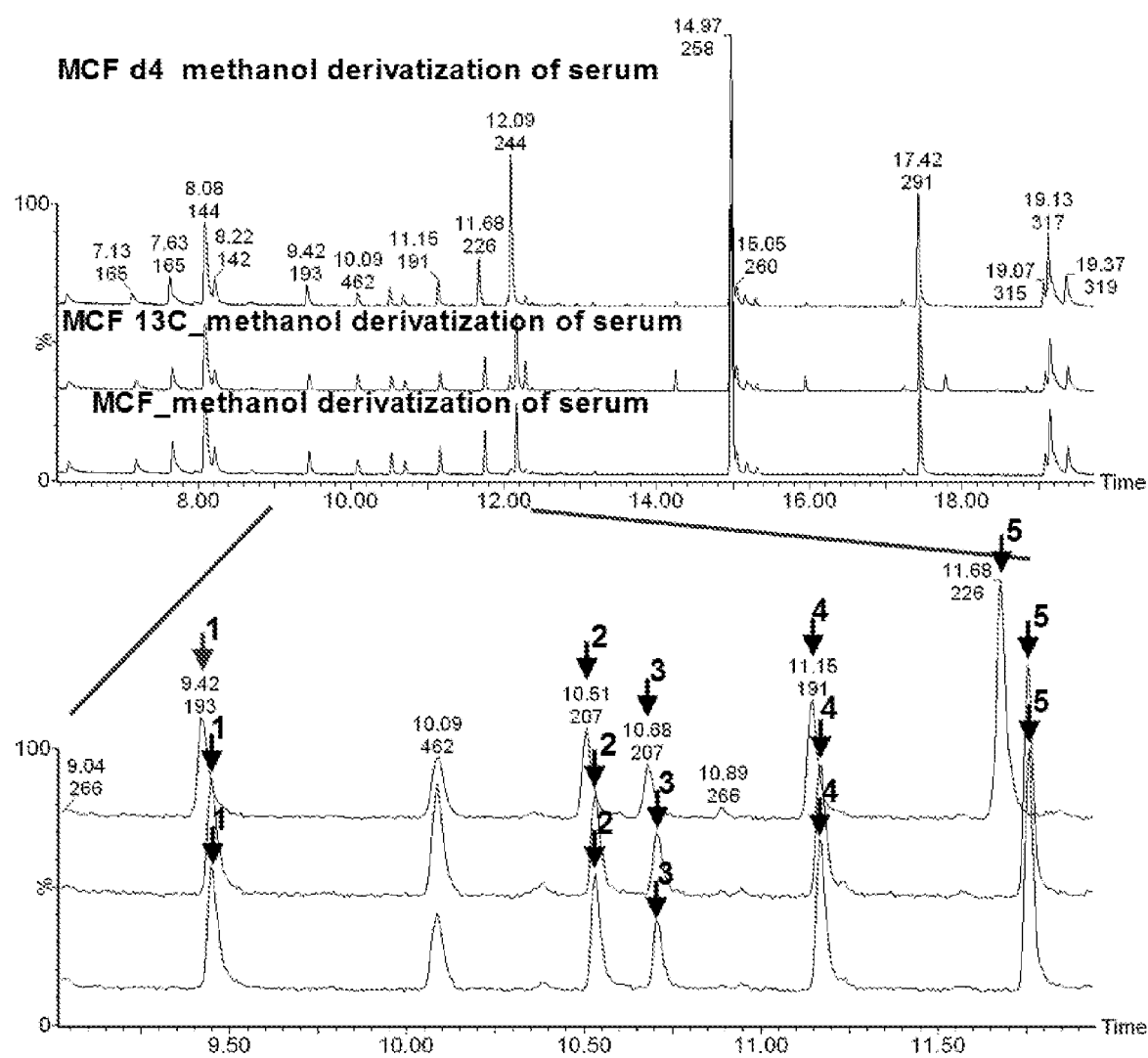
FIG. 2. Advantages of $^{13}C$ labeling, and disadvantages of deuterated reagent labeling for acyl chloroformate/alcohol derivatizations. Serum was purchased from Santa Cruz. Total ion chromatogram (TIC) in the Electron Impact Ionization (EI) mode reveals no retention time shifts of peaks from samples derivatized with unlabeled methylchloroformate (MCF)/methanol derivatization (bottom) vs. unlabeled MCF with $^{13}C$ labeled methanol (middle row). However, retention time shifts were seen for both vs. samples derivatized with unlabeled MCF and deuterated methanol (top row). The results reveal a retention time shift with the use of deuterated methanol in MCF derivatized samples. The bottom figure is enlarged between the retention times of 9 to 12 minutes. The peaks marked with the same number beside the arrows from top to bottom were confirmed from the mass spectrum to be the same metabolites for labeled methanol, or unlabeled methanol, in the MCF/methanol derivatization.
Figure 3A:
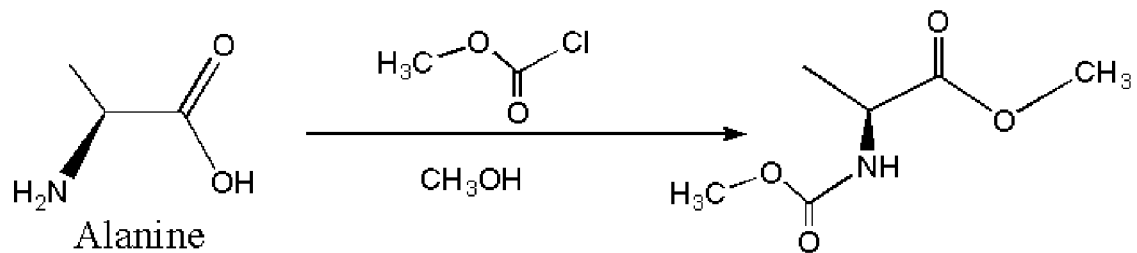
FIG. 3A. L-Alanine, derivatized by unlabeled MCF and methanol resulting in L-Alanine, N-methyoxycarbonyl-methyl ester. Formula: $C_6H_{11}NO_4$, MW 161, Exact Mass 161.068808, NIST #313387.
Figure 3B:
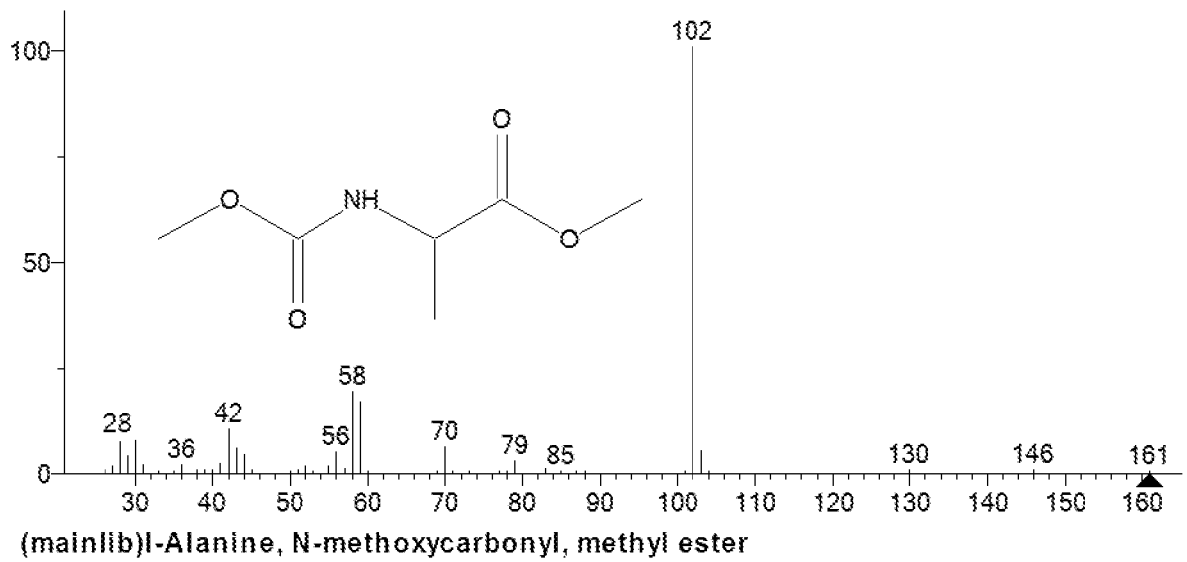
FIG. 3B. EI Spectra of L-Alanine, N-methyoxycarbonyl-methyl ester. For the 10 largest peaks, m/z=102 is the base peak. In terms of the percentage of the base peak, the peak at m/z 58 is 19.1% of the base peak, m/z 59 is 16.5%, m/z 42 is 10.3%, m/z 30 is 7.5%, m/z 28 is 7.4%, m/z 70 is 6.2%, m/z 43 is 5.7%, m/z 103 is 5.2%, and m/z 56 is 5% of the base peak.
Figure 3C:
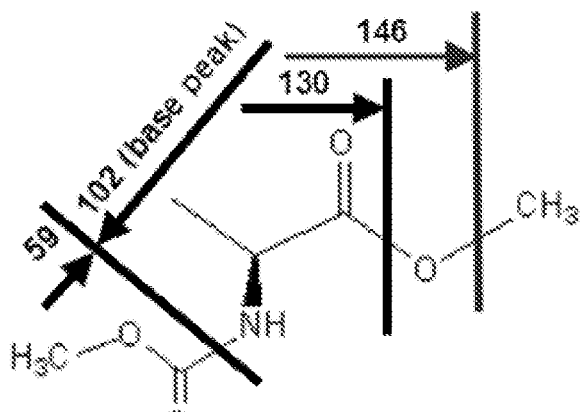
FIG. 3C. Diagram of Electron Ionization (EI) fragmentation of alanine derivatized by unlabeled methylchoroformate and methanol.
Figure 3D:
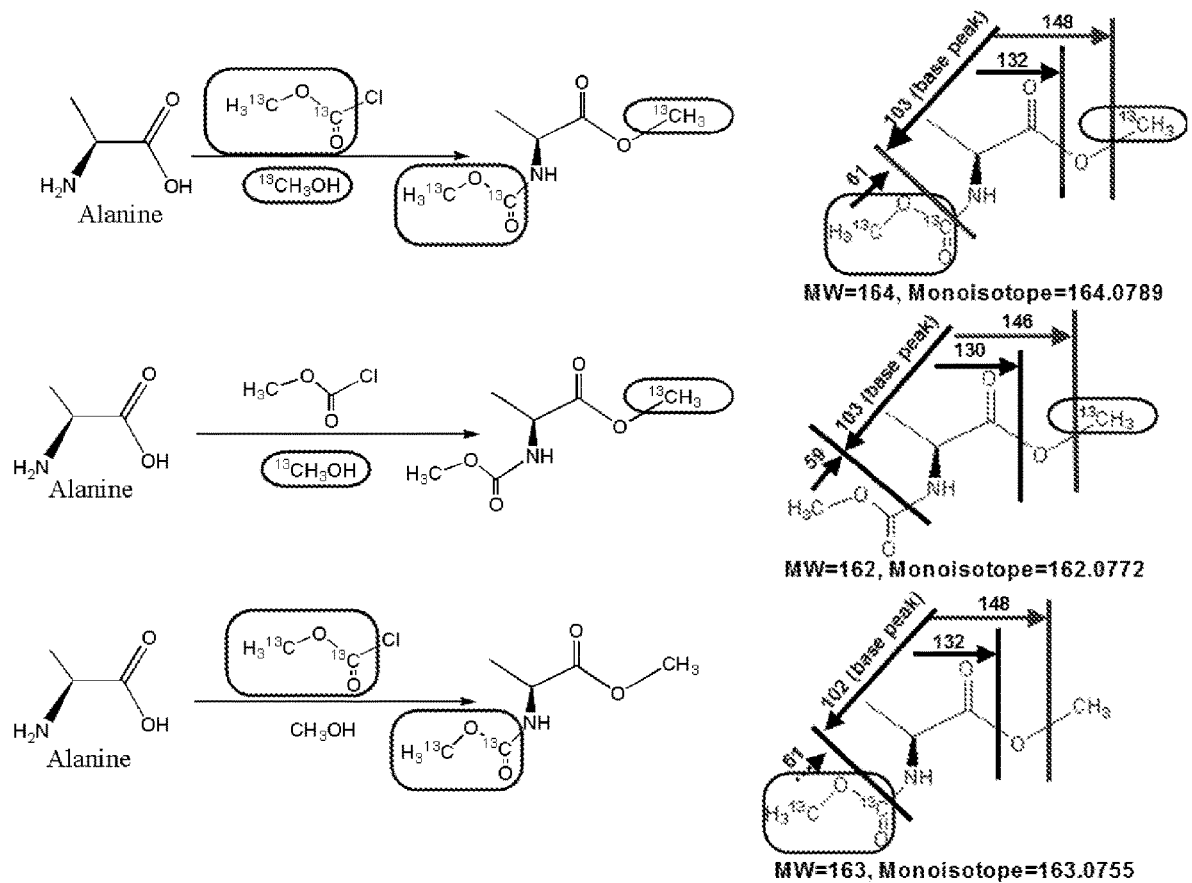
FIG. 3D. Use of derivatization by $^{13}C$ acyl chloroformates and $^{13}C$ alcohols for directed positional labeling of alanine. Shown are diagrams of EI fragmentation of directed positional labeling of alanine, when $^{13}C$ labeled methanol and $^{13}C$ methylchlorformate are used together or separately.
Figure 3E:
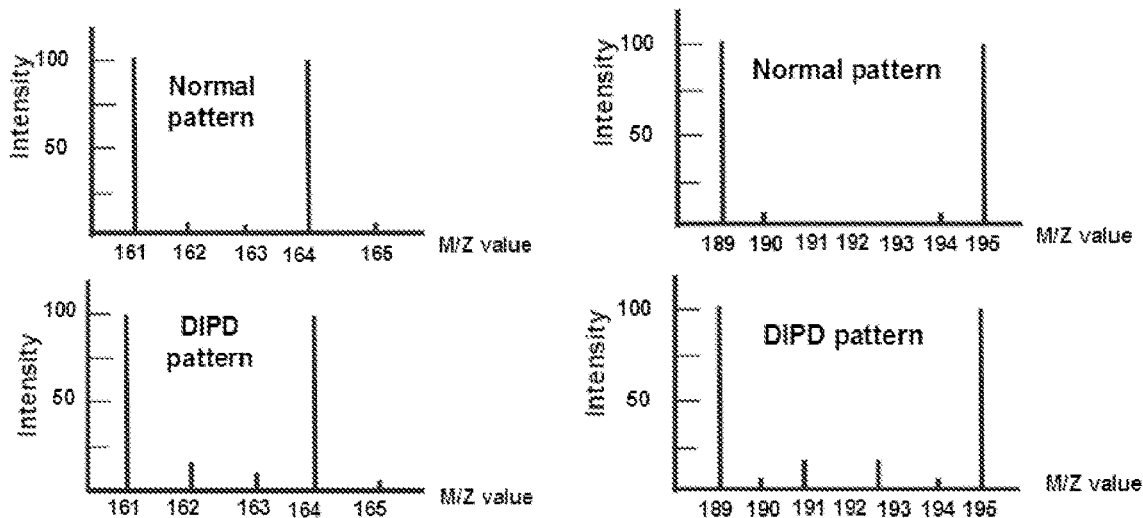
FIG. 3E The Directed Isotopic Positional Derivatization (DIPD) approach. Mixing the M1/M0 DIPD experiment for singly labeled methylchloroformate or $^{13}C$ methanol 1:1 with the products of the Mn−1/Mn DIPD experiment using doubly labeled methylchloroformate (left panel) results in a characteristic "DIPD barcode" pattern, as does the M0+2/M0 and Mn−2/Mn DIPD experiment, using fully labeled $^{13}C$ methylchloroformate and fully labeled $^{13}C$ ethanol (right panel), and their unlabeled $^{12}C$ counterparts, which is done if the baseline M1 or Mn−1 peak is high.
Figure 4A:
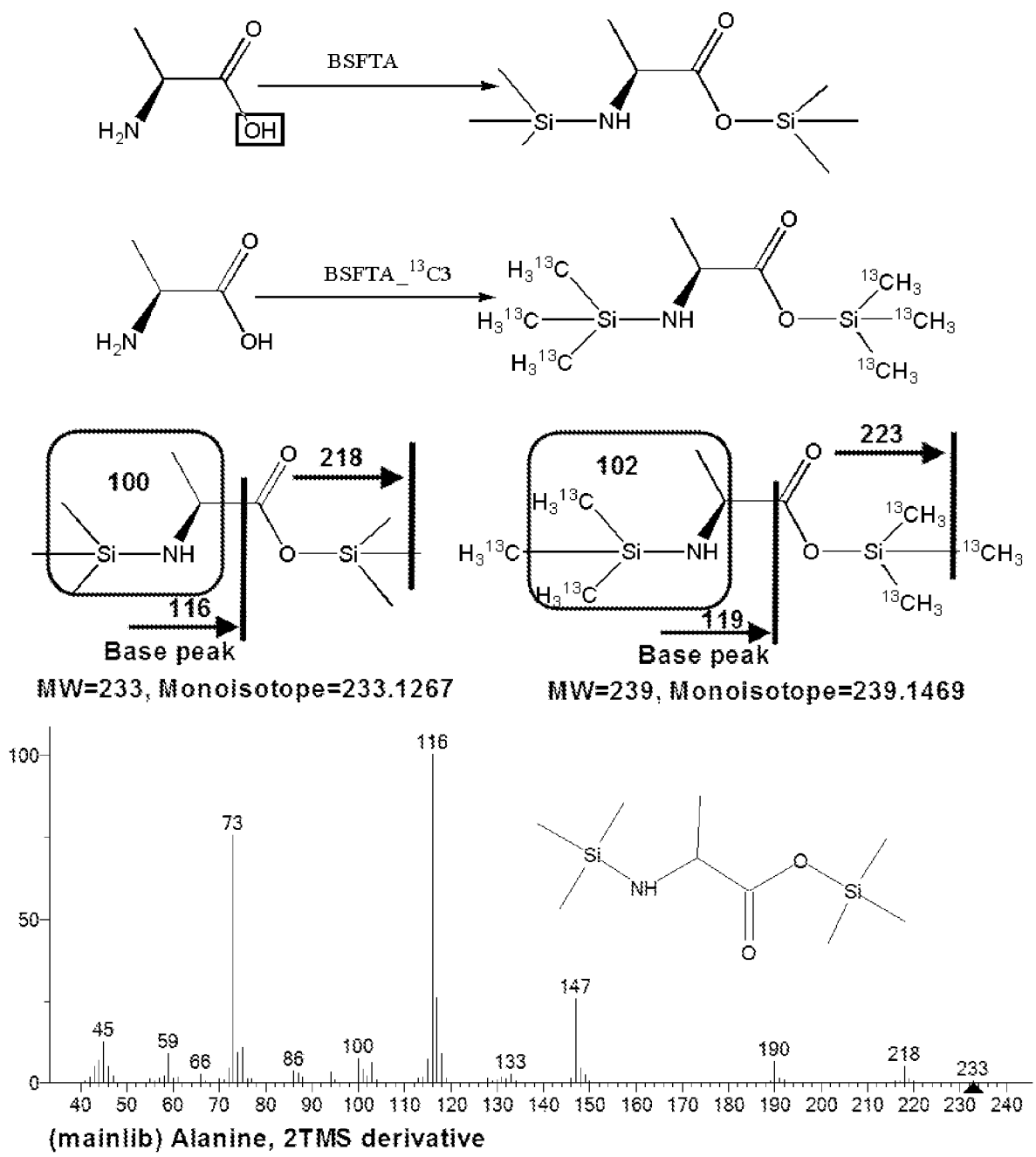
FIG. 4A. Use of $^{13}C$ labeled silylation reagents for amino vs carboxylic group identification, showing use of $^{13}C$ BSTFA for derivatization of alanine. Characteristic ion is at 116 m/z for unlabeled BSTFA derivatization of alanine, and 119 m/z for $^{13}C$ BSTFA derivatization. NIST EI fragmentation shown for unlabeled BSTFA derivatization of alanine. Formula: $C_9H_{23}NO_2Si_2$, MW 233, Exact Mass 233.126732, NIST #2899-44-7. For the 10 largest peaks, m/z=116 is the base peak. In terms of the percentage of the base peak, the peaks at m/z 73 is 75.1%, m/z 11.7 is 25.7%, m/z 147 is 25.3%. m/z 45 is 12.4%, m/z 75 is 10.5%, m/z 74 is 9.0%, m/z 59 is 8.9%, m/z 118 is 8.999%, and m/z 100 is 7.4%.
Figure 4B:
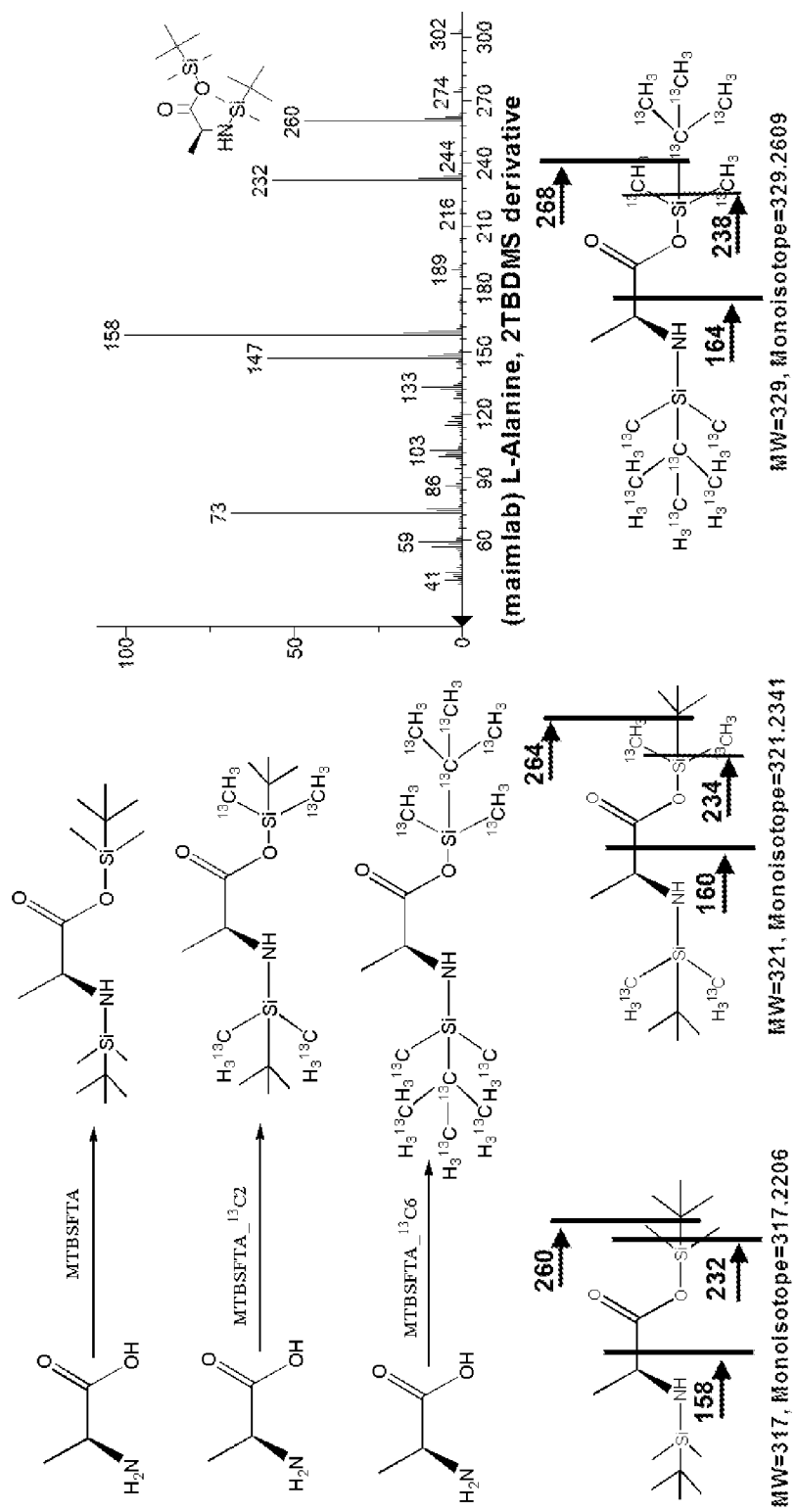
FIG. 4B. Use of $^{13}C$ labeled MTBSTFA for derivatization of alanine. Characteristic ion is at 158 m/z for unlabeled MTBSTFA derivatization of alanine, 160 m/z for MTBSTFA derivatization containing two $^{13}C$ methyl groups, and 164 m/z for alanine derivatized with uniformly labeled $^{13}C$ MTBSTFA. Formula: $C_{15}H_{35}NO_2Si_2$, MW 317, Exact Mass 317.220633, NIST #92751-15-0. For the 10 largest peaks, m/z=158 is the base peak. In terms of the percentage of the base peak, the peaks at m/z 73 is 68.2%, m/z 147 is 57.6%, m/z 232 is 56.0%. m/z 260 is 46.5%, m/z 159 is 17.0%, m/z 59 is 12.7%, m/z 233 is 12.6%, m/z 133 is 11.8%, and m/z 261 is 10.8%.
Figure 6A:
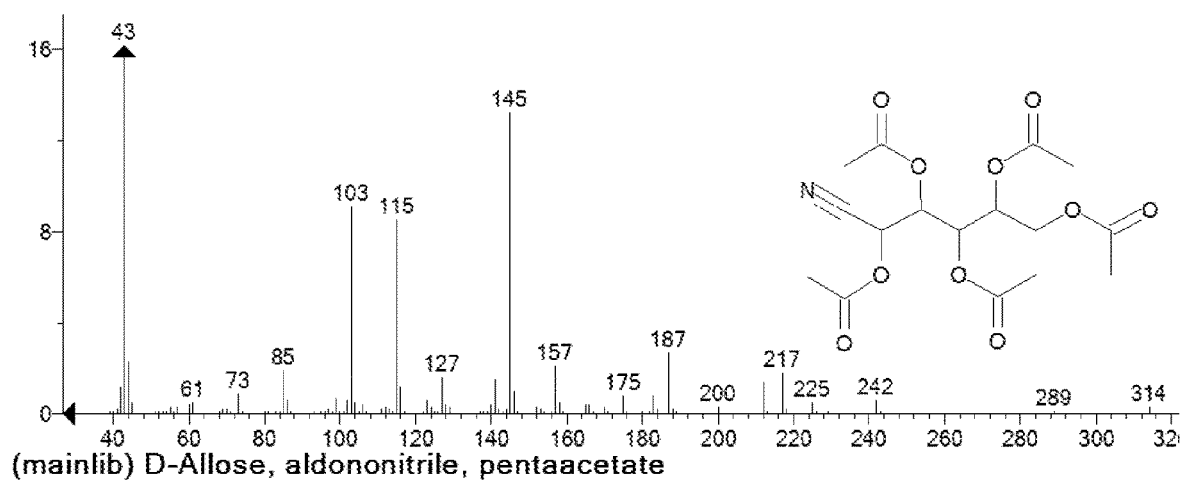
FIG. 6A. EI spectra of glucose aldonitrile pentaacetetate derivatives, showing unlabeled glucose aldonitrile and unlabeled penta-acetate derivative. D-Allose, aldononitrile, pentaacetate, Formula: $C_{16}H_{21}NO_{10}$, MW: 387 Exact Mass: 387.116547 NIST#: 380429 ID#: 12421, Non-stereo. For the 10 largest peaks, m/z=43 is the base peak. In terms of the percentage of the base peak, the peaks at m/z 145 is 14.1%, m/z 103 is 9.7%, m/z 115 is 9.1%, m/z 187 is 2.8%, m/z 44 is 2.4%, m/z 157 is 2.2%, m/z 85 is 2.0%, m/z 217 is 1.9%, and m/z 127 is 1.7%.

The disadvantages of using deuterated GC/MS derivatization reagents (deuterated BSFTA, deuterated methylchloroformate, deuterated methanol) are shown in FIGS. 1 and 2. The expected results for Electron Impact Ionization with unit Dalton resolution GC/MS for unlabeled vs. labeled derivatization (DIPD) reagents are shown in FIGS. 3, 4 and 6. FIG. 7A shows an algorithm, using high resolution GC/MS, to chemically characterize the reactive groups targeted by DIPD reagents on unknown metabolites, to easily discriminant chemical class(es) from the background of all detectable metabolites, and to quantitate all members of chemical classes derivatized by DIPD reagents.

$^{13}$C Methyl chloroformate/$^{13}$C methanol and $^{13}$C ethylchloroformate/$^{13}$C ethanol reagents (and other matched acyl chloroform and alcohol derivatization reagents), in combination with chemical profiling done with $^{13}$C acetic anhydride, have distinct advantages for the characterization of chemicals that could also be analyzed by silylation and use of deuterated derivatization reagents that can presently be purchased. FIG. 1 shows the alterations in peak shape, and retention time shifts, for sample derivatization for deuterated (d9) vs unlabeled BSTFA. FIG. 2 shows the alterations in peak shape, and retention time shifts for NIST1950 plasma derivatized with deuterated (d4) methanol. With d9 BSTFA the retention time shifts and peak shape changes can be dramatic, due to the 9 deuteriums labeling each reactive chemical group (hydroxyl, thiol, amino, imino, carboxyl and phosphate groups), with less dramatic changes seen with derivatization with d4 methanol, as only 3 deuteriums associated with the methyl group label, and only carbonyl groups are derivatized.

Compared with chemicals derivatized with deuterated reagents, FIG. 2 illustrates that chemicals that are labeled with $^{13}$C show no shift in retention time relative to the unlabeled chemicals, and no distortion of their peak shape, enabling accurate quantitation of chemical spectra, since time alignment of chemical labeled with $^{12}$C vs. $^{13}$C is precise.

The versatility for the use of acyl chloroformate, with matching alcohol for derivatization, both for quantitation and unknown chemical identification, is illustrated in FIG. 3 for methylchloroformate paired with methanol using L-Alanine as an example. The methyl chloroformate derivatization reaction requires both methyl chloroformate and methanol. FIG. 3 shows how directed isotopic positional derivation (DIPD) labeling aids chemical identification of the carbonyl- vs. amine groups on the derivatized alanine using $^{13}$C labeled methylchloroformate with unlabeled methanol to identify the amine groups, or $^{13}$C methanol with unlabeled methylchloroformate to identify the carbonyl groups. Derivatization of alanine is shown as an example, as it has both an amine and a carboxylic group. The carboxylic acid group acquires a methyl from the methanol forming an ester, and the amine group becomes a carbamate from the methylchloroformate. The $^{13}$C from either the methanol or the methylchloroformate can be uniquely detected under electron Impact ionization (EI) GC/MS. The carbamate fragment has a m/z of 59 when unlabeled, and 61 when its has incorporated two $^{13}$C atoms from $^{13}$C labeled methylchloroformate. The rest of the derivatized alanine forms the characteristic ion, m/z 102 unlabeled, with m/z of 103 with the carbonyl group is labeled by $^{13}$C methanol. If both $^{13}$C labeled methylchloroformate is used together with $^{13}$C methanol, the presence of the labeled carbamate can be discerned by the mass difference between the m/z 130 unlabeled EI fragment (FIG. 3C) and the m/z 132 fragment which has the carbamate from the $^{13}$C labeled methylchloroformate, but not the methyl group from the $^{13}$C methanol (FIG. 3D). The presence of the labeled methyl group from the $^{13}$C methanol is discerned from the comparison of the unlabeled m/z 102 characteristic ion (EI) fragment (FIG. 3C) to any of the other conditions containing $^{13}$C methanol (m/z 103, FIG. 3C), as this fragment has the carbamate group sheared off. FIG. 3E illustrates the Directed Isotopic Positional Derivatization (DIPD) approach. Mixing the M1/M0 DIPD experiment for singly labeled methylchloroformate or $^{13}$C methanol 1:1 with the products of the Mn−1/Mn DIPD experiment using doubly labeled methylchloroformate (left panel) results in a "DIPD spectral barcode" characteristic pattern, as does the M0+2/M0 and Mn−2/Mn DIPD experiment, using fully labeled $^{13}$C methylchloroformate and fully labeled $^{13}$C ethanol, and their unlabeled $^{12}$C counterparts, which is done if the baseline M1 or Mn−1 peak is high.

For discrimination of the metabolites for DIPD chemical class(es) vs the background, the M1/M0, and the Mn−1/Mn ratio can be set with the appropriate ratio of unlabeled to labeled DIPD reagents. For example, if $^{13}$C methylchloroformate was labeled only on one carbon, and mixed with $^{13}$C methanol, in a 9:1 (M0/M1) ratio of fully unlabeled ($^{12}$C methylchloroformate and $^{12}$C methanol): singly $^{13}$C labeled methylchloroformate derivatization of alanine, the DIPD spectral barcode pattern will show a significant increase in the M0+1 peak by CI (162) as well as increasing the EI peak intensities at 60, 131, and 146. For unknowns having amine, but no carboxyl groups, only an increase in M0+1 intensity will be seen for the amine group. To set the Mn−1/Mn ratio you would mix 9:1 fully labeled $^{13}$C methylchlorformate and $^{13}$C methanol with singly labeled $^{13}$C methyl chloroformate and unlabeled methanol. Mixing the M0/M1 DIPD experiment 1:1 with the products of the Mn−1/Mn DIPD experiment results in a "DIPD spectral bar code" characteristic pattern, shown for alanine in the left panel of FIG. 3E for CI and EI. Alternatively, one could examine the M0+2/M0 and Mn−2/Mn DIPD ratio experiment, if the baseline M1 or Mn−1 peak is high with methylchloroformate and methanol DIPD reagents. To do this you would just need, for example, fully labeled $^{13}C$ ethylchloroformate and fully labeled $^{13}C$ ethanol, and their unlabeled $^{12}C$ counterparts. For the M0/M0+2 DIPD ratio mix 9:1 unlabeled ethylchloroformate and ethanol: to an equal amount of either fully labeled $^{13}C$ ethylchloroformate to unlabeled ethanol, or mix 9:1 unlabeled ethylchloroformate and ethanol: fully labeled $^{13}C$ ethanol to unlabeled ethylchloroformate, for derivation. For the Mn-2/Mn DIPD ratio, mix 9:1 fully labeled $U^{13}C$ ethylchloroformate and fully labeled $^{13}C$ ethanol to $U^{13}C$ ethylchloroformate and unlabeled ethanol. For alanine, when the results of the M0+2/M0 DIPD ratio experiment are mixed with the Mn-2/Mn DIPD ratio experiment, a "DIPD spectral bar code" spectral pattern occurs, which flags the DIPD metabolite, and aids in identification (right panel, FIG. 3E).

For FIG. 4, the same amino and carboxylic groups on alanine are labeled and identified under EI using $^{13}C$ labeled BSTFA, or $^{13}C$ MTBSTFA.

Figure 5:
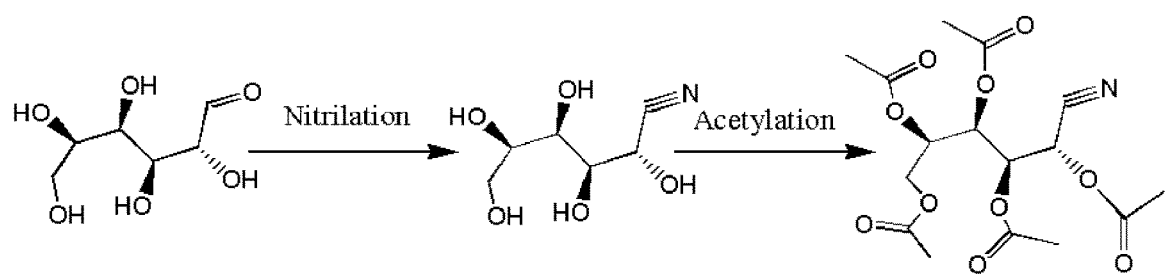
FIG. 5. Illustration of formation of aldodnitrile pentaacetate glucose derivative by nitrilation, and acetylation by acetic anhydride.

FIGS. 5 and 6 illustrates OH group labeling with $^{13}C$ acetic anhydride for sugars such as glucose, a very specific reaction.

For quantitation of unlabeled metabolites with $^{13}C$ labeled derivatization reagents, first a quality control sample would be made from the sample set, and the QC represents the average value of all the metabolites in a data set, or can be a standardized (for example NIST supplied) tissue sample, or standardized mix of QC compounds aimed at reproducing the targeted biofluid or tissue profile. The QC sample would be derivatized with $^{13}C$ labeled reagents (99% $^{13}C$) and added back at a 1:1 volume with each sample, or the DIPD protocol would allow the normalization of the M0 intensity by the Mn intensity, for example for alanine, with the M0 (for ex., unlabeled methylchlorformate and methanol) normalized by M3 ($U^{13}C$ methylchloroformate and $U^{13}C$ methanol, see left panel FIG. 3E).

For methylchloroformate use for determining the number of reactive groups, the sample would be derivatized with $^{13}C$ methylchloroformate and $^{13}C$ methanol, or $^{13}C$ methylchloroformate and unlabeled methanol, or unlabeled methylchloroformate and $^{13}C$ methanol. The sample would also be derivatized with unlabeled derivatization reagents. The number of amine or carboxyl groups derivatized would be determined from the mass shift difference seen on CI. For, example, when a sample derivatized with $^{13}C$ methylchloroformate and $^{13}C$ methanol, and combined with a sample derivatized with unlabeled methylchloroformate and unlabeled methanol, the algorithm would identify alanine on CI from a mirror pair (same retention time) of m/z 164 (alanine derivatized with $^{13}C$ methylchloroformate and $^{13}C$ methanol reagents) and m/z 161 (alanine derivative with unlabeled reagents). The algorithm assesses this as there is one $^{13}C$ labeled on the carboxyl ester, and the remaining 2 m/z difference is due the 1 amine group labeled with 2 $^{13}C$ s present on the carbamate. This identification would be confirmed with EI, with ions 59, 102, 130 and 146 seen for alanine derivatized with unlabeled methylchloroformate and unlabeled methanol, and EI ions 61, 103, 132, 148 with alanine derivatized by 99%+$^{13}C$ methylchloroformate and 99%+$^{13}C$ methanol.

For quantitation, the QC sample derivatized with both $^{13}C$ labeled methylchloroformate used together with $^{13}C$ methanol, and the exact registration of all chromatographic peaks makes it possible to normalize using the characteristic ion intensity, for all metabolites in the database. For alanine would be EI peak 103 from labeled reagents for normalization, and sample peak EI 102 from unlabeled reagents.

Figure 6B:
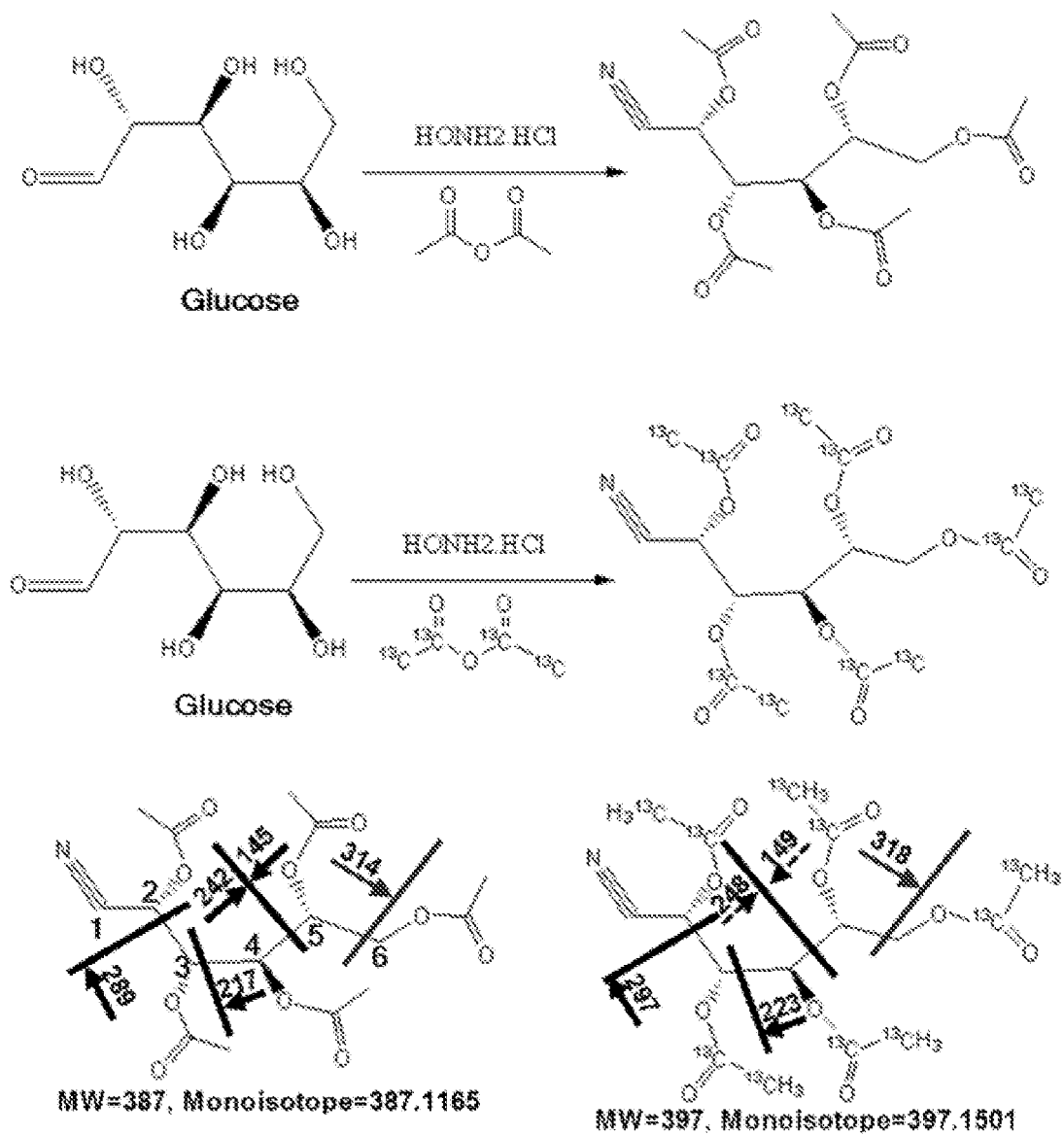
FIG. 6B. Unlabeled glucose aldonirtrile and $^{13}C$-labeled penta-acetate derivative. Diagram explaining differences in EI fragmentation for unlabeled glucose aldonitrile penta-acetate vs $^{13}C$ glucose aldonitrile penta-acetate EI spectra.

Acetic anhydride acylation of sugar alcohols, ribose, deoxyribose, glycerol, lactate and bile acids is complementary to metabolite classes detected by methylchloroformate derivatization. The EI pattern allows one to see if there was complete acetylation, as seen for glucose derivatized with unlabeled reagents in FIG. 6A, and run under EI, the, C1-C4 fragment has m/z 241, C1-C5 fragment has m/z of 314 and C4-C6 fragment has m/z 217. FIG. 6B compares the EI fragmentations for glucose aldonitrile penta-acetate derivative using unlabeled vs labeled acetic anhydride. Note: the CI m/z for glucose aldonitrile pentaacetate is 331, so the CI mass shifts of labeled vs unlabeled QC derivatives also confirm the number of groups acetylated.

For known compounds, precise calibration of the metabolites can be had for plasma or serum by spiking the NIST 1950 plasma standard derivatized with both 99%+$^{13}C$ methylchloroformate and 99%+ methanol, or 99% acetic anhydride, as many values for this plasma standard have been quantitated (Simón-Manso et al. [1]).

For metabolites not in the software database, quantitation can still be done, just the identity is not immediately apparent. Elucidation of the identities of unknown metabolites can be facilitated, if high resolution GC/MS or LC/MS are used. FIG. 7A illustrates how the use of high resolution GC/MS and the information obtained from the $^{13}C$ labeling pattern of the molecular ion using chemical ionization (CI), as well as the $^{13}C$ labeling pattern from electron impact ionization (EI) fragmentation, can be used to narrow the number of possible chemical formulae, reinforcing the FIG. 3 illustration of how DIPD reagents can be used for detection and quantification.

Figure 7B:
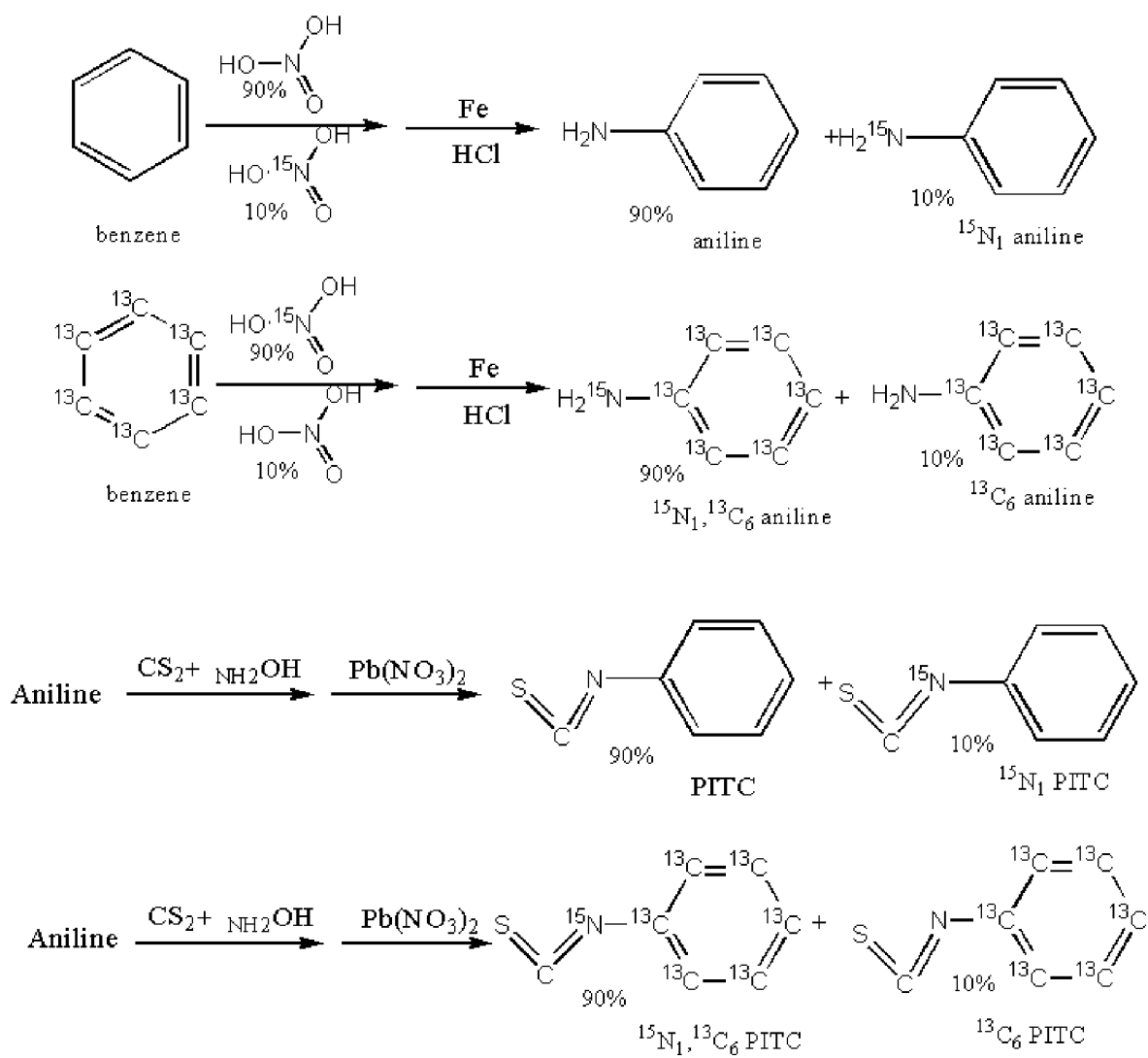
FIG. 7B. Cost effective manufacture of the labeled aniline and phenylisothiocyanate (PITC) reagents to be used in the DIPD relative and absolute metabolite quantification kit for LC/MS. Starting with separate reactions with unlabeled ($^{12}C$) benzene and $U^{13}C$ benzene, the unlabeled benzene is reacted with 10% $^{15}N$ nitric acid and 90% unlabeled nitric acid, and the $U^{13}C$ benzene is reacted with 90% $^{15}N$ nitric acid and 10% unlabeled nitric acid. The aniline products of these reactions are further reacted with $CS_2$, $NH_2OH$ and $Pb(NO_3)_2$ to form PITC labeled identically in the same proportions as the aniline products of the above benzene reactions (9:1 unlabeled PITC: $^{15}N_1$ $^{12}C_7$ PITC and 9:1 $^{15}N_1$ $^{13}C_6$ PITC: $^{14}N_1$ $^{13}C_6$ PITC).

FIG. 7B shows how a DIPD framework can be designed for PITC, starting with the manufacture of the labeled DIPD M0/M1, and Mn/Mn-1 DIPD reagents. Starting with separate reactions with unlabeled ($^{12}C$) benzene and $U^{13}C$ benzene, the unlabeled benzene is reacted with 10% $^{15}N$ nitric acid and 90% unlabeled nitric acid, and the $U^{13}C$ benzene is reacted with 90% $^{15}N$ nitric acid and 10% unlabeled nitric acid. The aniline products of these reactions are further reacted with $CS_2$, $NH_2OH$ and $Pb(NO_3)_2$ to form PITC labeled identically in the same proportions as the aniline products of the above benzene reactions (9:1 unlabeled PITC: $^{15}N_1$ $^{12}C_6$ PITC and 9:1 $^{15}N_1$ $^{13}C_6$ PITC: $^{14}N_1$ $^{13}C_6$ PITC).

Figure 7C:
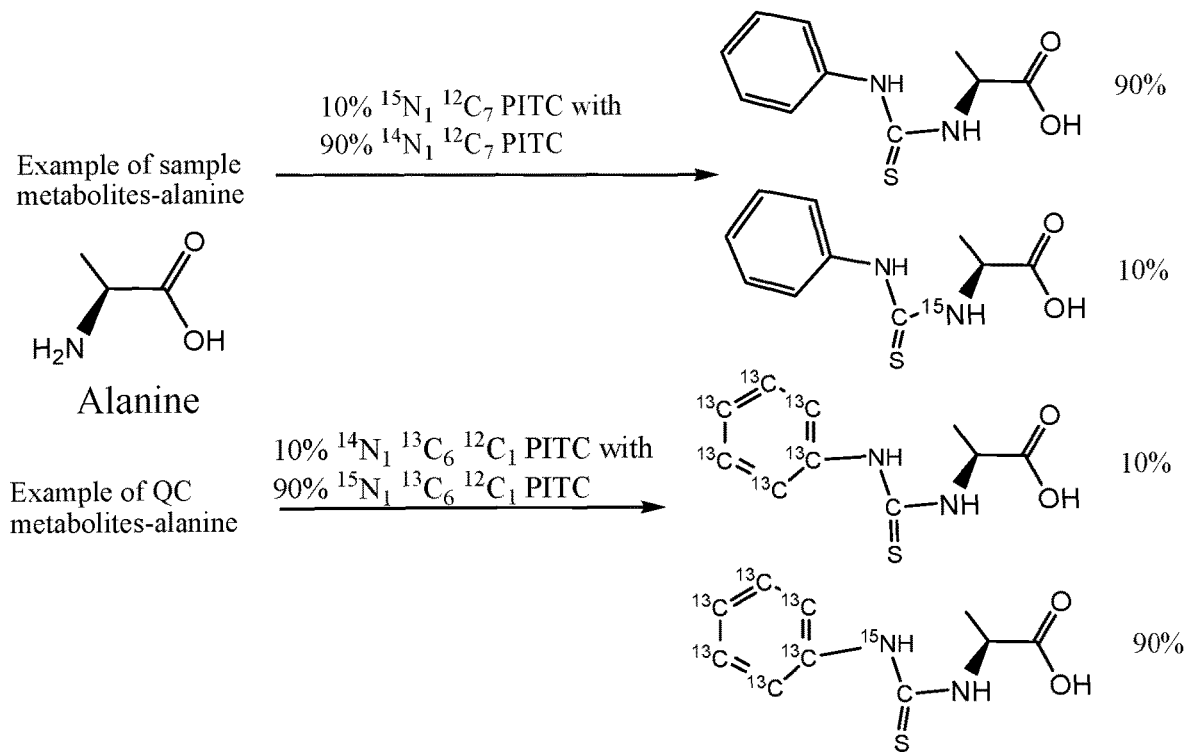
FIG. 7C. Demonstrates how phenylisothiocyanate (PITC), which labels nitrogens on amines and amino acids, can be used in a DIPD framework to detect known and unknown amine/amino acid metabolites in high resolution LC/MS. The M1/M0 DIPD ratio can be determined by derivatizing the sample with 9:1 unlabeled PITC: $^{15}N_1$ $^{12}C_7$ PITC and the Mn−1/Mn DIPD ratio can uniquely be obtained using a quality control (QC) sample, generated from the experiment or standardized for tissue or biofluid, by derivatizing the QC with 9:1 $^{15}N_1$ $^{13}C_6$ PITC: $^{14}N_1$ $^{13}C_6$ PITC. This yields both identification by chemical class (recognition of the M1/M0 and Mn−1/Mn DIPD ratios), and relative quantitation, by dividing the M0 PITC derivatized intensity by the Mn PITC derivatized QC intensity for each metabolite in the sample.

FIG. 7C demonstrates how phenyl isothiocyanate (PITC), which labels nitrogens on amines and amino acids, can be used in a DIPD framework to detect known and unknown amine/amino acid metabolites in high resolution LC/MS. The M0/M1 DIPD ratio can be determined by derivatizing the sample with 9:1 unlabeled PITC: $^{15}N_1$ $^{12}C_6$ PITC and the Mn/Mn-1 DIPD ratio can uniquely be obtained using a quality control (QC) sample, generated from the experiment or standardized for tissue or biofluid, by derivatizing the QC with 9:1 $^{15}N_1$ $^{13}C_6$ PITC: $^{14}N_1$ $^{13}C_6$ PITC. The M0/M0+1 and Mn/Mn-1 DIPD experiments can then be mixed 1:1 and combined, forming a characteristic "DIPD spectral barcode pattern that can identify the metabolite. This yields both identification by chemical class (recognition of the M0/M1 and Mn/Mn-1 DIPD ratios), and relative quantitation, by dividing the M0 PITC derivatized intensity by the Mn PITC derivatized intensity for each metabolite in the sample. The M0 and Mn-1 peak heights have ~doubled (bottom panel) with respect to the unlabeled PITC derivatized alanine (top panel). Note: The kit will also contain a tube with hundreds+ metabolites, characteristic of a particular biofluid or tissue, whose concentrations can be used for absolute quantification of these targets. First, you would combine the M0/M1

(PITC) derived sample 1:1 with the Mn/Mn-1 QC, to get both identification and quantification of all metabolites in the sample relative to the QC levels. Then as a last experiment you would derivatize the QC with M0 and M1 (PITC) reagents and the known standards mix with Mn-1 and Mn (PITC reagents), to find the actual concentrations of targets in the QC, and then backcalculate the concentrations of all these targets in the samples.

Figure 7D:
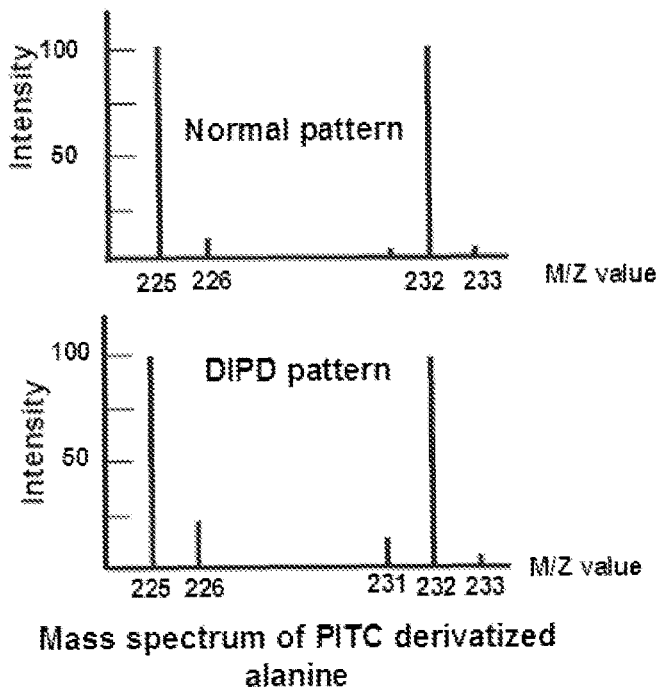
FIG. 7D. Example of the spectrum for alanine treated by DIPD, with 9:1 unlabeled PITC: $^{15}N_1$ $^{12}C_7$ PITC combined with 9:1 $^{15}N_1$ $^{13}C_6$ PITC: $^{14}N_1$ $^{13}C_6$ PITC in the bottom panel and alanine treated with unlabeled PITC combined with $^{15}N_1$ $^{13}C_6$ PITC only for the top panel experiment. The M1/M0 and Mn−1/Mn ratios have ~doubled (bottom panel) with respect to the unlabeled and $^{15}N_1$ $^{13}C_6$ PITC derivatized alanine (top panel), illustrating how the DIPD spectral barcode increases signal to noise for the M1/M0 and Mn−1/Mn ratios, which can be detected by specially designed software.

FIG. 7D Example of the spectrum for alanine treated by DIPD, with 9:1 unlabeled PITC: $^{15}N_1$ $^{12}C_6$ PITC combined with 9:1 $^{15}N_1$ $^{13}C_6$ PITC:$^{14}N_1$ $^{13}C_6$ PITC in the bottom panel and alanine treated with unlabeled PITC combined with $^{15}N_1$ $^{13}C_6$ PITC only for the top panel experiment. The M1/M0 and Mn-1/Mn ratios have ~doubled (bottom panel) with respect to the unlabeled and $^{15}N_1$ $^{13}C_6$ PITC derivatized alanine (top panel). There is a clear enhancement of the M0/M1 and Mn-1/Mn ratios for the DIPD experiment (lower panel), illustrating how the DIPD spectral barcode increases signal to noise for the M1/M0 and Mn-1/Mn ratios, which can be detected by specially designed software.

Figure 7E:
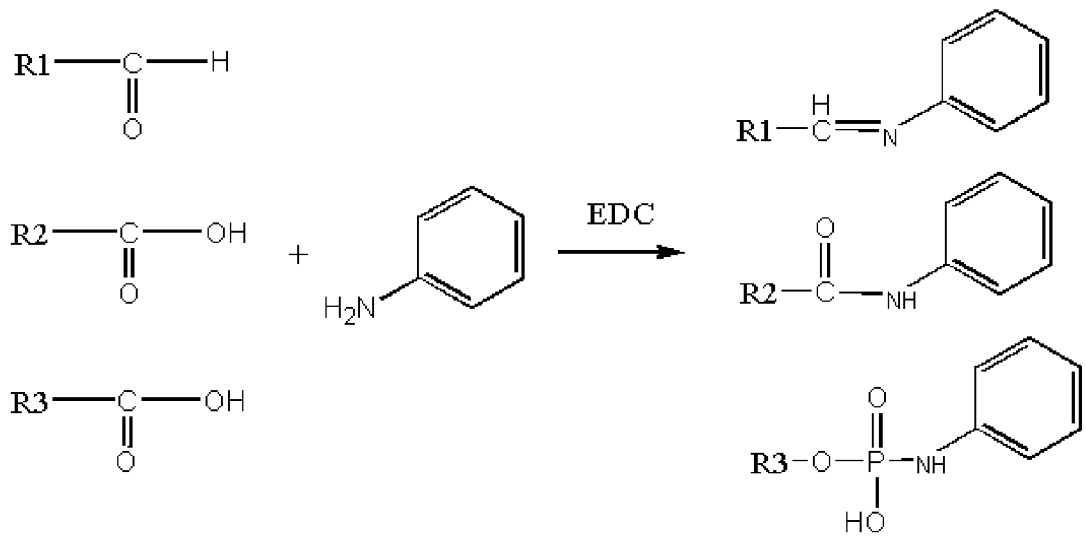
FIG. 7E. General labeling reactions for carbonyl, carboxyl and phosphoryl groups with aniline.

FIG. 7E. General labeling reactions for carbonyl, carboxyl and phosphoryl groups with aniline, indicating the versatility of the DIPD aniline reagents. Between the DIPD aniline reagents, and DIPD PITC reagents, hundreds to thousands of potential small molecules can be labeled.

Figure 7F:
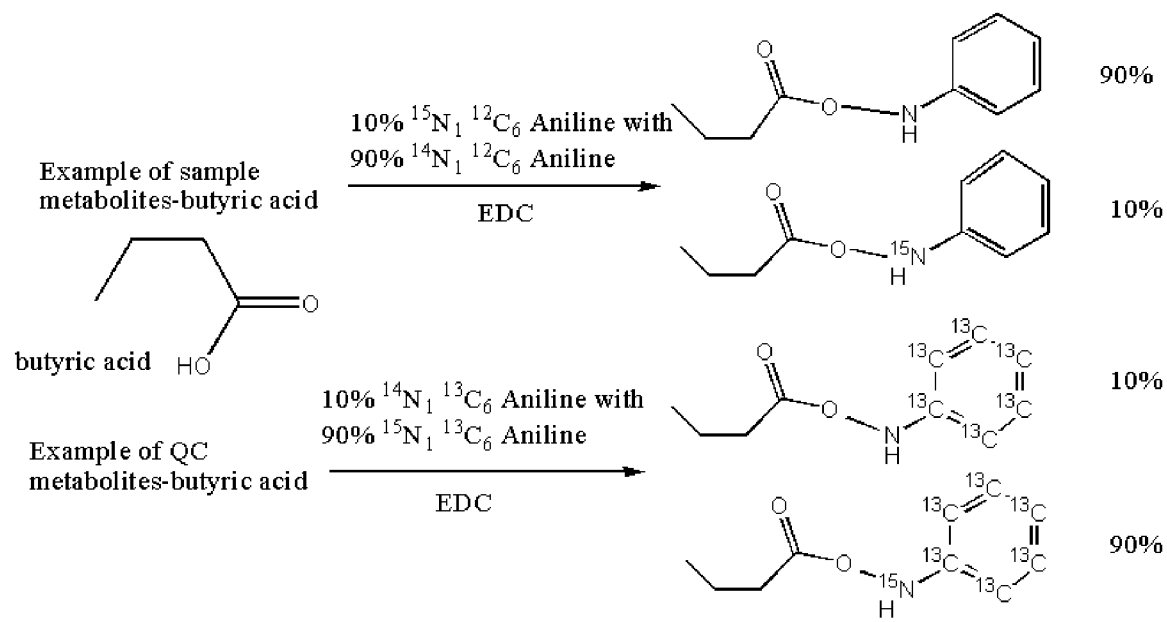
FIG. 7F. A detailed example of metabolite labeling reactions for butyric acid and aniline DIPD reagents. The DIPD reagent contains M0 and M1 reagents (9:1 unlabeled aniline: $^{15}N_1$ $^{12}C_6$ aniline) and Mn and Mn−1 (9:1 $^{15}N_1$ $^{13}C_6$ aniline: $^{14}N_1$ $^{13}C_6$ aniline) reagents. For determining the M1/M0 DIPD ratio, there are 10% enrichment in the M1 reagent ($^{15}N_1$ $^{12}C_6$ aniline) with 90% natural abundance for the M0 ($^{14}N_1$ $^{12}C_6$ aniline) reagent. For determining the Mn−1/Mn DIPD ratio, there are 10% M6 (Mn−1) ($^{14}N_1$ $^{13}C_6$ aniline) reagent with 90% fully labeled M7 (Mn) ($^{15}N_1$ $^{13}C_6$ aniline) reagent. M1 and Mn−1 can be generated from alterations in the nitrogen label or the carbon label. The figure assumes the change is in nitrogen label, which may be easier to manufacture than altering the abundance of one $^{13}C$ in the benzene ring.
Figure 7G:
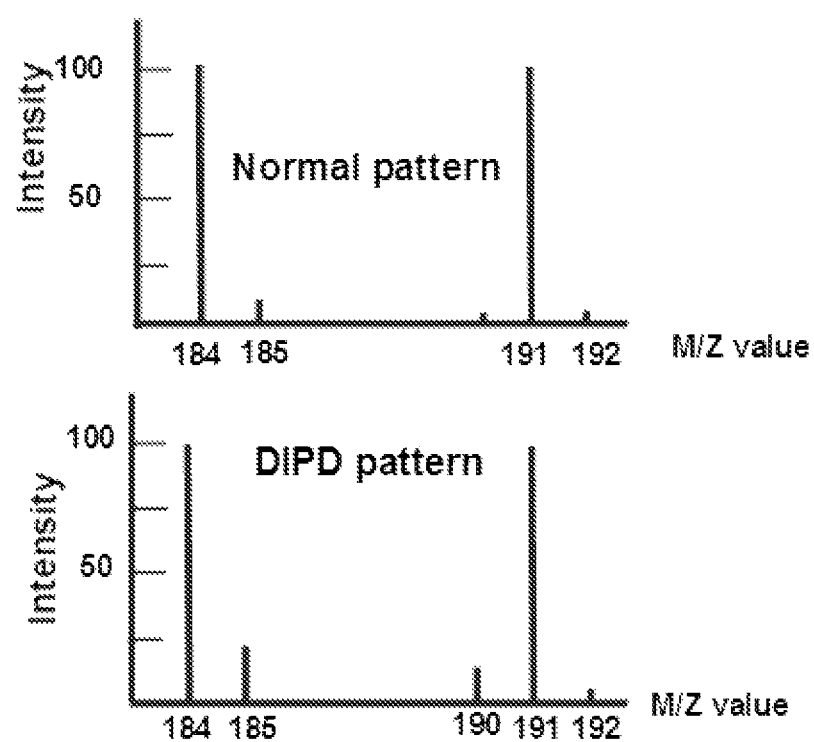
FIG. 7G. DIPD barcode mass spectrum derived from the reaction of DIPD aniline M0 and M1 reagents (M0/M1 9:1 natural abundance ($^{14}N_1$ $^{12}C_6$) aniline: $^{15}N_1$ $^{12}C_6$ aniline) and Mn and Mn−1 (Mn/Mn−1 9:1 $^{15}N_1$ $^{13}C_6$ aniline: $^{14}N_1$ $^{13}C_6$ aniline) reagents with butyric acid (FIG. 7F). The upper spectrum shows the spectrum pattern of 1:1 mixture of derivatized butyric acid with natural abundance aniline, and 99% $^{13}C$ and $^{15}N$ labeled aniline ($^{15}N_1$ $^{13}C_6$ aniline). The lower spectrum shows DIPD pattern which derives from 1:1 mixture of 10% M1/M0, and 10% Mn−1/Mn aniline (n=number of labeled atoms, including $^{13}C$ and $^{15}N$). In the normal pattern where butyric acid was derivatized with natural abundance aniline, there is about 11% Mo/M1 intensity, which is similar to any other compound or artifacts with 10 carbons, and about a 5% Mn−1/Mn intensity. The DIPD barcode mass spectral pattern has about 21% M1/M0 intensity and about 15% Mn−1/Mn intensity, greatly increasing the signal to noise ratio, and produces a special pattern which can be recognized by specially designed software.

FIG. 7F shows a detailed example of metabolite labeling reactions for butyric acid and aniline DIPD reagents. The DIPD reagent contains M0 and M1 reagents (9:1 unlabeled aniline: $^{15}N_1$ $^{12}C_6$ aniline) and Mn and Mn-1 (9:1 $^{15}N_1$ $^{13}C_6$ aniline: $^{14}N_1$ $^{13}C_6$ aniline) reagents. For determining the M0/M0+1 DIPD ratio, there are 10% enrichment in the M1 reagent ($^{15}N_1$ $^{12}C_6$ aniline) with 90% natural abundance ($^{14}N_1$ $^{12}C_6$ aniline) reagent. For determining the Mn/Mn-1 DIPD ratio, there are 10% Mn-1 ($^{14}N_1$ $^{13}C_6$ aniline) reagent with 90% fully labeled ($^{15}N_1$ $^{13}C_6$ aniline) reagent. M1 and Mn-1 can be generated from nitrogen label or carbon label. The Mn/Mn-1 DIPD ratio in FIG. 7G can reflect the change in nitrogen label $^{14}N_1$ vs. $^{15}N_1$, which is easier to manufacture DIPD reagents for. The DIPD barcode mass spectrum derived from the reaction of DIPD aniline M0 and M1 reagents (9:1 natural abundance aniline: $^{15}N_1$ $^{12}C_6$ aniline) and Mn and Mn-1 (9:1 $^{15}N_1$ $^{13}C_6$ aniline: $^{14}N_1$ $^{13}C_6$ aniline) reagents with butyric acid is shown in FIG. 7G. The upper spectrum shows the spectrum pattern of 1:1 mixture of derivatized butyric acid with natural abundance aniline, and 99% $^{13}C$ and $^{15}N$ labeled aniline ($^{15}N_1$ $^{13}C_6$ aniline). The lower spectrum shows DIPD pattern which derives from 1:1 mixture of 10% M1/M0, and Mn-1/Mn aniline (n=number of labeled atoms, including $^{13}C$ and $^{15}N$). In the normal pattern where butyric acid was derivatized with natural abundance aniline, there is about 11% M1/M0 intensity, which is similar to any other compound or artifacts with 10 carbons, and about a 5% Mn-1/Mn intensity. The aniline DIPD butyric acid barcode mass spectral pattern has about 21% M1/M0 intensity and about 15% Mn-1/Mn intensity, greatly increasing the signal to noise ratio, and produces a special pattern which can be recognized by specially designed software.

FIG. 7G contains an example of increased metabolite discrimination with DIPD reagents (M1/M0 and M7/M6 patterns vs M0 and M7 patterns alone). In FIG. 7G, DIPD barcode mass spectrum derived from the reaction of DIPD aniline M0 and M1 reagents (9:1 natural abundance aniline: $^{15}N_1$ $^{12}C_6$ aniline) and Mn and Mn-1 (9:1 $^{15}N_1$$^{13}C_6$ aniline: $^{14}N_1$ $^{13}C_6$ aniline) reagents with butyric acid (FIG. 7F). The upper spectrum shows the spectrum pattern of 1:1 mixture of derivatized butyric acid with natural abundance aniline, and 99% $^{13}C$ and $^{15}N$ labeled aniline ($^{15}N_1$ $^{13}C_6$ aniline). The lower spectrum shows DIPD pattern which derives from 1:1 mixture of 10% M1/M0, and Mn-1/Mn (M6/M7) aniline (n=number of labeled atoms, including $^{13}C$ and $^{15}N$). In the normal pattern where butyric acid was derivatized with natural abundance aniline, there is about 11% M0/M1 intensity, which is similar to any other compound or artifacts with 10 carbons, and about a 5% M6/M7 intensity. The DIPD barcode mass spectral pattern has about 21% M1/M0 intensity and about 15% M6/M7 intensity, greatly increasing the signal to noise ratio, and produces a special pattern which can be recognized by specially designed software.

Figure 7H:
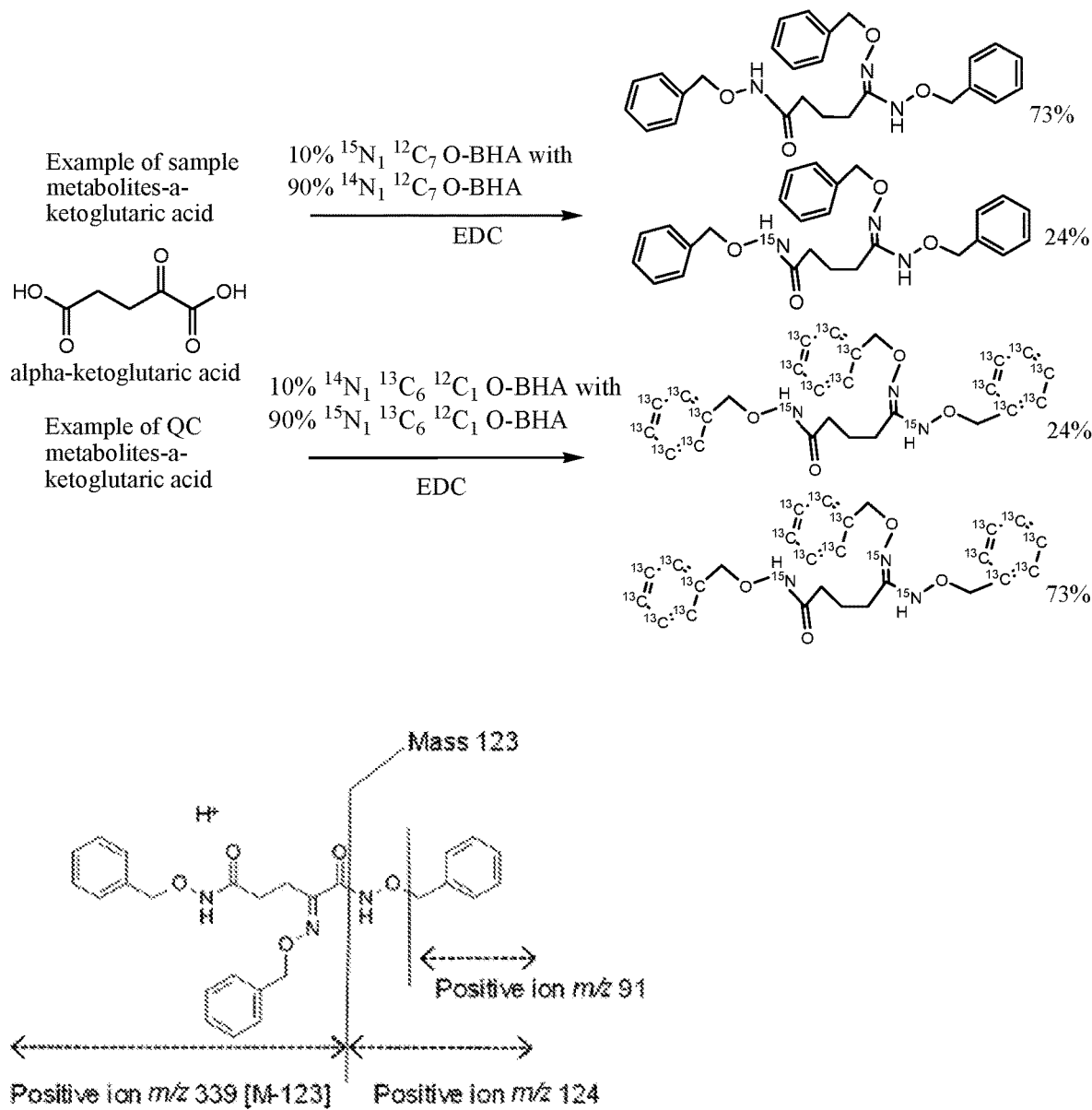
FIG. 7H The derivatization O-benzylhydroxylamine (o-BHA) and alpha-ketoglutaric (α-KG) acid (top panel) and the fragmentation scheme for O-benzylhydroxylamine (o-BHA) derivatized metabolites (bottom panel). Top panel: when 10% $^{15}N_1$ O-BHA were mixed with unlabeled O-BHA to derivatize α-ketoglutaric acid in samples, there will be about 73% unlabeled α-KG, 24% M1 α-KG derivatives, and 3% M2 α-KG derivatives. Similarly, when 10% $^{14}N_1$$^{13}C_6$$^{12}C_1$ O-BHA was mixed with 90% $^{15}N_1$$^{13}C_6$$^{12}C_1$ o-BHA to derivatize α-ketoglutaric acid in QC samples, there will be about 73% M21 (Mn) α-KG (three o-BHA molecule attached to each α-KG molecule, with each $^{15}N_1$$^{13}C_6$$^{12}C_1$ o-BHA adding 7 Da compared with unlabeled o-BHA), 24% M20 (Mn−1) α-KG derivatives, and 3% M19 (Mn−2) α-KG derivatives. The fragmentation scheme for O-benzylhydroxylamine (o-BHA) derivatized metabolites, shown for α-ketoglutarate derivatized with o-BHA ($^{14}N_1$ o-BHA, natural abundance product) is specific for carbonyl and carboxyl groups, and so 3 sites on alpha ketoglutarate were derivatized. $^{15}N_1$ o-BHA, $^{15}N_1$ $^{13}C_6$ o-BHA, and $^{14}N_1$ $^{13}C_6$ o-BHA would have the characteristic fragment losses of m/z 125, 131, and 130, respectively vs. m/z 124 for $^{14}N_1$ o-BHA, the natural abundance product.
Figure 7I:
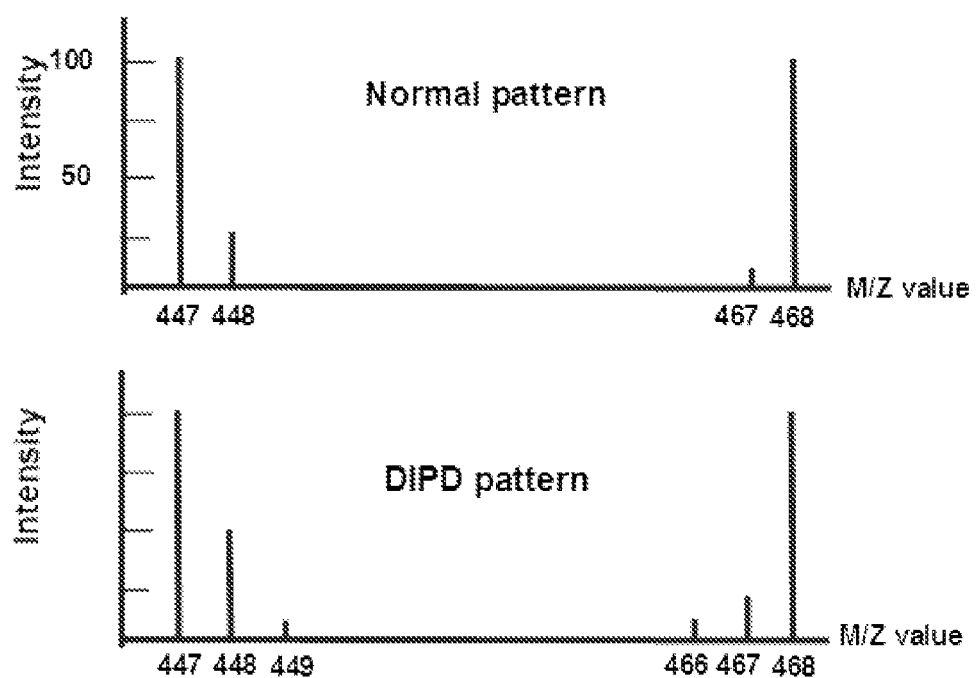
FIG. 7I. DIPD mass spectral barcode pattern of o-BHA derivatized alpha-ketoglutaric acid.

FIGS. 7H and 7I illustrate the uniqueness of DIPD reagent use (o-BPA) for detection of both the molecular ions (M1/M0 and Mn-1/Mn) and the characteristic ion fragmented from the DIPD metabolite. FIG. 7H The derivatization O-benzylhydroxylamine (o-BHA) and alpha-ketoglutaric (α-KG) acid. Top panel: when 10% $^{15}N$ o-BHA was mixed with unlabeled o-BHA to derivatize alpha-ketoglutaric acid in samples, there will be about 73% unlabeled α-KG, 24% M1 □-KG derivatives, and 3% M2 α-KG derivatives. Similarly, when 10% $^{14}N_1$$^{13}C_6$$^{12}C_1$ o-BHA was mixed with 90% $^{15}N_1$$^{13}C_6$$^{12}C_1$ o-BHA to derivatize α-ketoglutaric acid in QC samples, there will be about 73% M21 (Mn) α-KG (three O-BHA molecules attached to each α-KG molecule, each $^{15}N_1$$^{13}C_6$$^{12}C_1$ o-BHA molecule added 7 Da compared with unlabeled O-BHA=21 dalton shift for Mn), 24% M20 (Mn-1) α-KG derivatives, and 3% M19 (Mn-2) α-KG derivatives. The fragmentation scheme for O-benzylhydroxylamine (o-BHA) derivatized metabolites, shown for alpha ketoglutarate (FIG. 7H), o-BHA ($^{14}N_1$ O-BHA, natural abundance product) is specific for carbonyl and carboxyl groups, and so 3 sites on alpha ketoglutarate were derivatized. $^{15}N_1$ o-BHA, $^{15}N_1$ $^{13}C_6$ o-BHA, and $^{14}N_1$ $^{13}C_6$ o-BHA would have the characteristic fragment losses of m/z 125, 131, and 130, respectively vs. m/z 124 for $^{14}N_1$ o-BHA, the natural abundance product (FIG. 7H). MS systems that allow global mining of parent and product ion data, such as the Sciex Triple TOF MS/MS$^{ALL}$ with SWATH acquisition mode and a window size of 21, would allow the confirmative recognition of M1/M0 and Mn-1/Mn (M20/M21) o-BHA DIPD α-KG barcode patterns, as all the M1/M0 and Mn-1/Mn (α-KG M20/M21) DIPD spectra could be found within one SWATH window, and molecular ion and characteristic fragments for the DIPD reagent used (see FIG. 7H,7I for o-BHA) would be seen.

DISCUSSION

The present invention addresses previously unmet needs in untargeted metabolomic profiling using the proposed Directed Isotopic Positional Derivatization (DIPD) reagents that include global quantitation of all derivatizable chemicals, global identification of all derivatizable chemicals in a sample from spectral databases, and elucidation of the chemical identities in a sample that have spectra not identifiable in known databases, in part by identifying reactive group identities on unknown chemicals that specifically interact with the DIPD reagents.

The invention works with low resolution (unit Dalton) single quadrupole GC/MS machines, which are the overwhelming majority of the installed GC/MS machines worldwide, for quantification, as well as triple quadrapole (unit dalton) LC/MS screening for both known and unknown chemicals and their quantitation.

When the invention is used with moderate to high resolution (10,000-120,000 resolution, GC/TOF MS, GC-Orbitrap MS, LC (liquid chromatography)/qTOF MS, LC Orbitrap MS)) or ultrahigh resolution (>240,000 resolution) LC/MS the invention aids in the identification of known and unknown metabolites, as well as their quantification using directed isotopic positional derivatization (DIPD) reagents. DIPD reagents can involve acyl chloroformates, alcohols, aniline, phenylisothiocyanate (PITC), O-benzylhydroxylamine (o-BHA) or others that a DIPD isotopic pattern can be generated with. Lipids may also be assessed with this DIPD approach, by the reactivity of TMS-$^{13}$CHN$_2$ for both phospholipids, sphingolipids, and smaller molecular weight compounds that can overlap with GC/MS characterization.

The invention described herein is ideal for quantification of all chemicals in a sample that can be analyzed by GC/MS and LC/MS. The sample does, or does NOT, have to come from biologic experiments that incorporate stable isotopes, any chemical, or tissue/biofluid extract is suitable, and the invention works with low resolution GC/MS, the overwhelming majority of the GC/MS machines installed worldwide, as well as medium to high resolution LC/MS machines (10,000 to 120,000 resolution). For GC/MS, the quantification method described in this invention using $^{13}$C derivatization reagents can be done in the chemical ionization (CI), or electron impact (EI) fragmentation mode of a single quadrapole GC/MS, which is a standardized mode for all GC/MS machines worldwide and for which all GC/MS databases have catalogued spectra. The EI spectra generated with this invention use common EI databases, such as NIST and Wiley, which contain over 1 million spectra, collectively. The invention can globally code large numbers of analytes for comparison between two samples, or a sample and its internal standard (IS) simultaneously, with precise retention time registration between the two samples (or IS) and no peak shape changes due to use of $^{13}$C labeling for the derivatization reagent instead of the commonly used deuterium labeling.

For LC/MS, DIPD reagents comprised of unlabeled and $^{13}$C and/or $^{15}$N aniline, phenylisothiocyanate (PITC) and O-benzylhydroxylamine (o-BHA) reagents can be used for the vast majority of small polar metabolites, covering compounds containing carbonyl, carboxyl, phosphoryl and amino/amine groups.

An advantage of the present invention is that since the $^{13}$C labeled derivatized metabolites exactly co-elute with the metabolites derivatized with unlabeled derivatization reagents, alignment of all samples having a similar matrix (plasma or urine or liver tissue as examples) occurs. Alignment of labeled and unlabeled derivatized metabolites with precise retention time registration is a key step for accomplishing quantification of each metabolite globally. In contrast, with deuterium labeled derivatization reagents, global chromatograph alignments between deuterated and non-deuterated metabolite derivatives are not possible for GC/MS, and are not a priori predictable for LC/MS, as it would depend on column chemistries. The DIPD approach allows for easy recognition/identification of chemicals containing reactive groups that can be derivatized by DIPD reagents, and aids their discrimination from background noise. Quantification, both relative to a QC standard or targeted for absolute levels to a metabolite mixture is part of the kit protocol, and quantification may have useful clinical applications.

REFERENCES

1 Simon-Manso, Y. et al. Metabolite profiling of a NIST Standard Reference Material for human plasma (SRM 1950): GC-MS, LC-MS, NMR, and clinical laboratory analyses, libraries, and web-based resources. *Analytical chemistry* 85, 11725-11731, doi: 10.1021/ac402503m (2013).

2 Mattingly, S. J., Xu, T., Nantz, M. H., Higashi, R. M. & Fan, T. W. A Carbonyl Capture Approach for Profiling Oxidized Metabolites in Cell Extracts. *Metabolomics* 8, 989-996, doi: 10.1007/s11306-011-0395-z (2012).

3 Zhao, S., Dawe, M., Guo, K. & Li, L. Development of High-Performance Chemical Isotope Labeling LC-MS for Profiling the Carbonyl Submetabolome. *Analytical chemistry* 89, 6758-6765, doi: 10.1021/acs.analchem.7b01098 (2017).

4 Guo, K. & Li, L. Differential 12C-/13C-isotope dansylation labeling and fast liquid chromatography/mass spectrometry for absolute and relative quantification of the metabolome. *Analytical chemistry* 81, 3919-3932, doi: 10.1021/ac900166a (2009).

5 Chan, J. C., Kioh, D. Y., Yap, G. C., Lee, B. W. & Chan, E. C. A novel LCMSMS method for quantitative measurement of short-chain fatty acids in human stool derivatized with (12)C- and (13)C-labelled aniline. *J Pharm Biomed Anal* 138, 43-53, doi: 10.1016/j.jpba.2017.01.044 (2017).

What is claimed is:

1. A method for metabolomic/lipidomic profiling of one or more compounds, by distinguishing signals of derivatives from background noise, in a biological sample comprising
A) i) derivatizing the one or more compounds with one or more $^{13}$C labeled or $^{15}$N labeled derivatization agents and one or more matching unlabeled derivatization reagents, wherein the ratio between the labeled derivatization reagents and matching unlabeled derivatization reagents is selected to enhance signal to noise ratio, wherein the $^{13}$C labeled or $^{15}$N labeled derivatization agents are selected from the group consisting of $^{13}$C methylchloroformate, $^{13}$C ethylchloroformate, $^{13}$C methanol, $^{13}$C ethanol, $^{13}$C acetyl anhydride, $^{13}$C labeled N,O-bis(trimethylsilyl)trifluoroacetamide (BSTFA), $^{13}$C labeled N-(tert.-butyldimethylsilyl)-N-methyl-trifluoroacetamide (MTBSTFA), trimethylsilyl-$^{13}$C-diazomethane (TMS-$^{13}$CHN$_2$), $^{13}$C and $^{15}$N phenylisothiocyanate (PITC), $^{13}$C and $^{15}$N aniline, and $^{13}$C and $^{15}$N O-benzylhydroxylamine; or ii) making two or more $^{13}$C labeled or $^{15}$N labeled standards for quantitating the one or more compounds by derivatizing the one or more compounds with two or more $^{13}$C labeled or $^{15}$N labeled derivatization reagents, wherein the ratio between the two or more derivatization reagents is selected to enhance signal to noise ratio, and introducing the $^{13}$C labeled or $^{15}$N labeled standards into a compound sample already derivatized with matching unlabeled derivatization reagents or $^{13}$C labeled or $^{15}$N labeled derivatization reagents;

and, for i) or ii), calculating the number of chemical groups on the molecule that can be derivatized, using chemical ionization (CI) and high resolution gas chromatography-mass spectroscopy (GC/MS), or for the molecular ion with LC/MS, from the mass shift from unlabeled reagents, aided globally from the exact registration of peaks between labeled and unlabeled reagents;

narrowing the chemical formulae possible for compounds not in a database; and comparing electron impact ionization (EI) spectra from matching $^{13}$C and $^{15}$N labeled barcode spectral patterns to reveal a composition of EI fragment identity to further aid chemical formulae identification;

comparing molecular ion and possibly MS/MS fragments generated by LC/MS to reveal a composition of MS/MS fragment identity to further aid chemical formulae identification; and B) i) for GC/MS, if amino group numbers need to be confirmed for an unknown compound, derivatizing the compounds containing the unknown with 99% $^{13}$C methylchloroformate (MCF) and unlabeled methanol vs. unlabeled MCF/methanol, wherein each 2 dalton mass shift seen on CI for each unknown represents one amino group;

comparing the EI spectra from matching unlabeled and labeled derivatization reagents to reveal composition of EI fragment identity to further aid chemical formulae identification; and comparing spectra with that from the sample derivatized with unlabeled silylation reagents to further narrow chemical formulae; and/or ii) if carboxyl group numbers need to be confirmed for an unknown compound, derivatizing the compounds containing the unknown with unlabeled methylchloroformate and 99% $^{13}$C methanol vs. unlabeled MCF/methanol, wherein each dalton mass shift seen on CI for each unknown represents one carboxyl group;

comparing EI spectra from matching unlabeled and labeled derivatization reagents to reveal composition of EI fragment identity to further aid chemical formulae identification; and comparing spectra with that from compounds derivatized with unlabeled silylation and/or MCF reagents to further narrow chemical formulae; and/or iii) if hydroxyl group numbers need to be confirmed for an unknown compound, derivatizing the compounds containing the unknown with 99% $^{13}$C acetic anhydride vs. unlabeled acetic anhydride, wherein each dalton mass shift on CI for each unknown represents one hydroxyl group;

iv) comparing EI spectra from matching unlabeled and labeled derivatization reagents to reveal composition of EI fragment identity to further aid chemical formulae identification; and v) comparing spectra with that from the sample derivatized with unlabeled silylation and/or MCF and methanol reagents to further narrow chemical formulae; and/or vi) determining the number of carbonyl, carboxyl, phosphoryl or amino/amine groups of a compound by assessing the molecular ion and/or MS/MS profiles by LC/MS using labeled reagents selected from the group consisting of $^{13}$C and $^{15}$N aniline, $^{13}$C and $^{15}$N PITC, and $^{13}$C and $^{15}$N o-BHA;

thereby metabolomic/lipidomic profiling one or more compounds in a biological sample.

2. The method claim 1, the $^{13}$C labeled or $^{15}$N labeled derivatization reagents of A)-ii) are selected from the group consisting of $^{13}$C methylchloroformate, $^{13}$C ethylchloroformate, $^{13}$C methanol, $^{13}$C ethanol, $^{13}$C acetyl anhydride, $^{13}$C labeled N,O-bis(trimethylsilyl)trifluoroacetamide (BSTFA), $^{13}$C labeled N-(tert.-butyldimethylsilyl)-N-methyl-trifluoroacetamide (MTBSTFA), trimethylsilyl-$^{13}$C-diazomethane (TMS-$^{13}$CHN$_2$), $^{13}$C and $^{15}$N PITC, $^{13}$C and $^{15}$N aniline, and $^{13}$C and $^{15}$N O-benzylhydroxylamine derivatizing compounds.

3. The method of claim 1, wherein the derivatizing reagents of A)-i) and A)-ii) comprise trimethylsilyl-$^{13}$C-diazomethane (TMS-$^{13}$CHN$_2$) which is used in connection with carboxyl and phosphate groups on the compounds.

4. The method of claim 1, wherein the derivatizing reagents are selected from the group consisting of $^{13}$C N,O-bis(trimethylsilyl)trifluoroacetamide (BSTFA), $^{13}$C N-(tert.-butyldimethylsilyl)-N-methyl-trifluoroacetamide (MTBSTFA), and trimethylsilyl-$^{13}$C-diazomethane (TMS-13CHN2).

5. The method of claim 1, wherein the $^{13}$C labeled or $^{15}$N labeled derivatization reagents comprise trimethylsilyl-$^{13}$C-diazomethane (TMS-$^{13}$CHN$_2$), and wherein the method comprises derivatizing the one or more compounds with TMS-$^{13}$CHN$_2$, and introducing the $^{13}$C labeled silylation standard into a compound sample derivatized with unlabeled TMS-CHN$_2$, and optionally then derivatizing these methylated compounds with one or more unlabeled derivatization silylation reagents.

6. The method claim 5, wherein the one or more unlabeled derivatization silylation reagents for derivatizing the methylated compounds are selected from the group consisting of N,O-bis(trimethylsilyl)trifluoroacetamide (BSTFA), N-(tert.-butyldimethylsilyl)-N-methyl-trifluoroacetamide (MTBSTFA), and N-Methyl-N-(trimethylsilyl) trifluoroacetamide (MSTFA).

7. The method of claim 1, wherein amino group numbers are confirmed for an unknown compound.

8. The method of claim 1, wherein carbonyl group numbers are confirmed for an unknown compound.

9. The method of claim 1, wherein hydroxyl group numbers are confirmed for an unknown compound.

10. The method of claim 1, wherein TMS-$^{13}$CHN$_2$ or other labeled reagents is used to create a $^{13}$C labeled silylation standard of one or more of compounds containing phosphate, COOH, aldehyde and/or amine groups.

11. The method of claim 10, wherein the one or more compounds are selected from the group consisting of sugars, glycolytic intermediates, organic acids/TCA cycle intermediates, amino acids, amines, fatty acids, eicosanoids/prostanoids; phospholipids/sphingolipids; phosphatidylinositol (PtdIns); and phosphorylated phosphoinisitides PtdIns3P, PtdIns4P, PtdIns5P, PtdIns(3,4)P$_2$, PtdIns(3,5)P$_2$, PtdIns(4,5)P$_2$ and PtdIns(3,4,5)P$_3$, phosphatidic acid (PA), phosphatidylserine (PS), phosphatidylcholine (PC), phosphatidylethanolamine (PE), phosphatidylglycerol (PG) and their lysophospholipids counterparts (LPC, -LPE, -LPS, -LPA, -LPG, and -LPI) and sphingomyelin.

12. The method of claim 1, wherein the $^{13}$C and $^{15}$N PITC is selected from the group consisting of $^{15}$N$_1$ $^{12}$C$_7$PITC, $^{15}$N$_1$$^{13}$C$_6$PITC and $^{14}$N$_1$ $^{13}$C$_6$PITC.

13. The method of claim 1, wherein the $^{13}$C and $^{15}$N aniline, is selected from the group consisting of $^{15}$N$_1$ $^{12}$C$_6$ aniline, $^{15}$N$_1$ $^{13}$C$_6$ aniline.

14. The method of claim 1, wherein the $^{13}$C and $^{15}$N 0-benzylhydroxylamine is selected from the group consisting of $^{15}$N$_1$ o-BHA, $^{15}$N$_1$$^{13}$C$_6$ o-BHA, and $^{14}$N$_1$$^{13}$C$_6$ o-BHA.

* * * * *